United States Patent
Kim et al.

(10) Patent No.: US 9,428,632 B2
(45) Date of Patent: Aug. 30, 2016

(54) QUATERNARY PHOSPHONIUM SALT, EPOXY RESIN COMPOSITION FOR ENCAPSULATING SEMICONDUCTOR DEVICE AND INCLUDING THE QUATERNARY PHOSPHONIUM SALT, AND SEMICONDUCTOR DEVICE ENCAPSULATED WITH THE EPOXY RESIN COMPOSITION

(71) Applicants: Min Gyum Kim, Uiwang-si (KR); Seung Han, Uiwang-si (KR); Hwan Sung Cheon, Uiwang-si (KR)

(72) Inventors: Min Gyum Kim, Uiwang-si (KR); Seung Han, Uiwang-si (KR); Hwan Sung Cheon, Uiwang-si (KR)

(73) Assignee: CHEIL INDUSTRIES, INC., Gumi-si, Kyeongsangbuk-do (KR)

( * ) Notice: Subject to any disclaimer, the term of this patent is extended or adjusted under 35 U.S.C. 154(b) by 48 days.

(21) Appl. No.: 14/069,564

(22) Filed: Nov. 1, 2013

(65) Prior Publication Data

US 2014/0179827 A1 Jun. 26, 2014

(30) Foreign Application Priority Data

Dec. 24, 2012 (KR) .................. 10-2012-0152620

(51) Int. Cl.
*C08L 63/00* (2006.01)
*H01L 23/29* (2006.01)
(Continued)

(52) U.S. Cl.
CPC .............. *C08K 5/50* (2013.01); *C07F 9/5442* (2013.01); *C08G 59/08* (2013.01); *C08G 59/621* (2013.01);
(Continued)

(58) Field of Classification Search
CPC ........................ C08G 59/688; C07F 9/5442
USPC .................................. 528/89; 568/9
See application file for complete search history.

(56) References Cited

U.S. PATENT DOCUMENTS

RE32,951 E * 6/1989 Whiteside et al. ............ 528/89
5,756,564 A * 5/1998 Murata ................. C08L 63/00
257/E23.119

(Continued)

FOREIGN PATENT DOCUMENTS

CN 101107285 A 1/2008
CN 101273076 A 9/2008
(Continued)

OTHER PUBLICATIONS

Alok R. Paital, et al., "Synthesis and structures of perthio- and polymeric metal complexes with the tetrathio- and dithioterephthalate ligands", Polyhedron 64 (2013) pp. 328-338.
(Continued)

*Primary Examiner* — Mark Kaucher
*Assistant Examiner* — Kregg Brooks
(74) *Attorney, Agent, or Firm* — Lee & Morse, P.C.

(57) ABSTRACT

A quaternary phosphonium salt, an epoxy resin composition including the quaternary phosphonium salt, and a semiconductor device encapsulated with the epoxy resin composition, the quaternary phosphonium salt being represented by Formula 1:

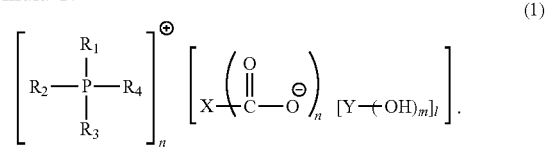

13 Claims, 1 Drawing Sheet

(51) Int. Cl.
*H01L 23/28* (2006.01)
*C08G 59/00* (2006.01)
*C08G 59/68* (2006.01)
*C09D 163/00* (2006.01)
*C07F 9/54* (2006.01)
*C08K 5/50* (2006.01)
*C08K 5/5419* (2006.01)
*C08G 59/08* (2006.01)
*C08G 59/62* (2006.01)

(52) U.S. Cl.
CPC ........... *C08G 59/688* (2013.01); *C08K 5/5419* (2013.01); *C08L 63/00* (2013.01); *H01L 23/295* (2013.01); *H01L 2924/0002* (2013.01)

(56) References Cited

U.S. PATENT DOCUMENTS

2006/0189721 A1* 8/2006 Akiyama et al. ............. 523/400
2009/0234080 A1 9/2009 Goh
2012/0046244 A1* 2/2012 Rogers et al. ................. 514/75

FOREIGN PATENT DOCUMENTS

| JP | 4153319 A | 5/1992 |
| JP | 5163335 A | 6/1993 |
| JP | 2006-307131 A | 11/2006 |
| WO | WO-2010/078300 A | 7/2010 |

OTHER PUBLICATIONS

Search Report mailed Apr. 29, 2014 in corresponding European Patent Application No. EP 13 19 0489.
Chinese Office Action dated Jun. 16, 2015 in Corresponding Chinese Patent Application No. 201310513314.7.

* cited by examiner

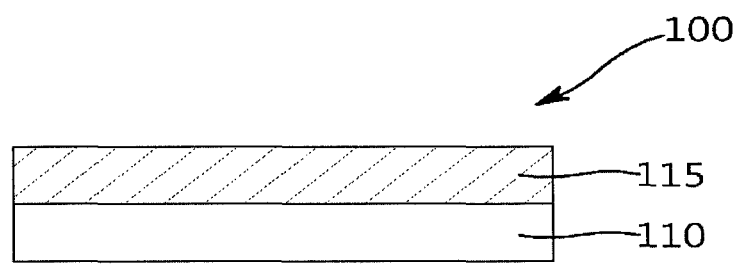

QUATERNARY PHOSPHONIUM SALT, EPOXY RESIN COMPOSITION FOR ENCAPSULATING SEMICONDUCTOR DEVICE AND INCLUDING THE QUATERNARY PHOSPHONIUM SALT, AND SEMICONDUCTOR DEVICE ENCAPSULATED WITH THE EPOXY RESIN COMPOSITION

CROSS-REFERENCE TO RELATED APPLICATION

Korean Patent Application No. 10-2012-0152620, filed on Dec. 24, 2012, in the Korean Intellectual Property Office, and entitled: "Quaternary Phosphonium Salt, Epoxy Resin Composition For Encapsulating Semiconductor Device Including The Quaternary Phosphonium Salt and Semiconductor Device Encapsulated With The Epoxy Resin Composition," is incorporated by reference herein in its entirety.

BACKGROUND

1. Field

Embodiments relate to a quaternary phosphonium salt, an epoxy resin composition for encapsulating a semiconductor device and including the quaternary phosphonium salt, and a semiconductor device encapsulated with the epoxy resin composition.

2. Description of the Related Art

Transfer molding may be used as a method of packaging semiconductor devices, e.g., ICs and LSIs, with epoxy resin compositions to obtain semiconductor modules, due to its advantages of low cost and suitability for mass production. For example, in transfer molding, modification of epoxy resins or phenolic resins as curing agents may lead to improvements in the characteristics and reliability of semiconductor modules.

SUMMARY

Embodiments are directed to a quaternary phosphonium salt, an epoxy resin composition for encapsulating a semiconductor device and including the quaternary phosphonium salt, and a semiconductor device encapsulated with the epoxy resin composition.

The embodiments may be realized by providing a quaternary phosphonium salt represented by Formula 1:

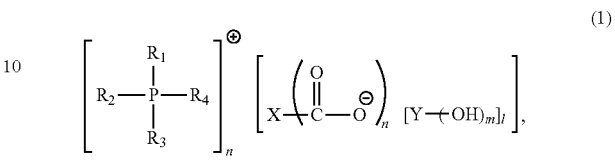

wherein $R_1$, $R_2$, $R_3$, and $R_4$ are each independently a substituted or unsubstituted $C_1$-$C_{30}$ hydrocarbon group or a substituted or unsubstituted $C_1$-$C_{30}$ hydrocarbon group including at least one heteroatom; X is a substituted or unsubstituted $C_1$-$C_{30}$ hydrocarbon group or a substituted or unsubstituted $C_1$-$C_{30}$ hydrocarbon group including at least one heteroatom; Y is a substituted or unsubstituted $C_1$-$C_{30}$ hydrocarbon group or Si substituted with one to three substituted or unsubstituted $C_1$-$C_{30}$ hydrocarbon groups; n and m are each independently an integer of 1 to 6, provided that when Y is Si, a sum of m and a number of substituents on the Si is a maximum of 4; and l is a number greater than 0 and up to 6.

$R_1$, $R_2$, $R_3$, and $R_4$ may each independently be a substituted or unsubstituted benzene group.

X may be a substituted or unsubstituted benzene group.

Y may be a substituted or unsubstituted benzene group, a substituted or unsubstituted naphthalene group, or Si substituted with one to three substituted or unsubstituted benzene groups.

n may be 2.

m may be 2 or 3.

l may be 2, 3, or 4.

The quaternary phosphonium salt may be represented by one of Formulae 1a to 1k:

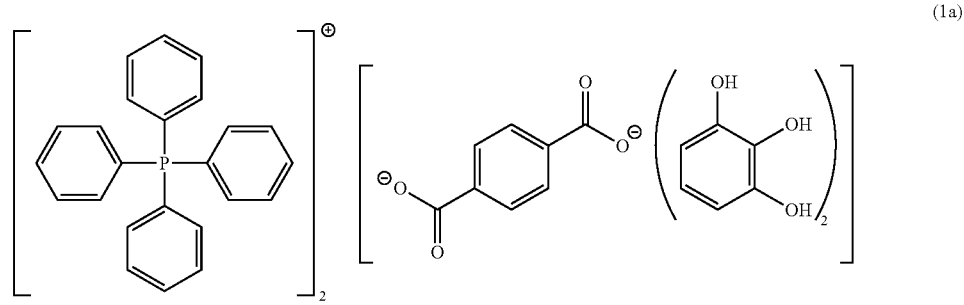

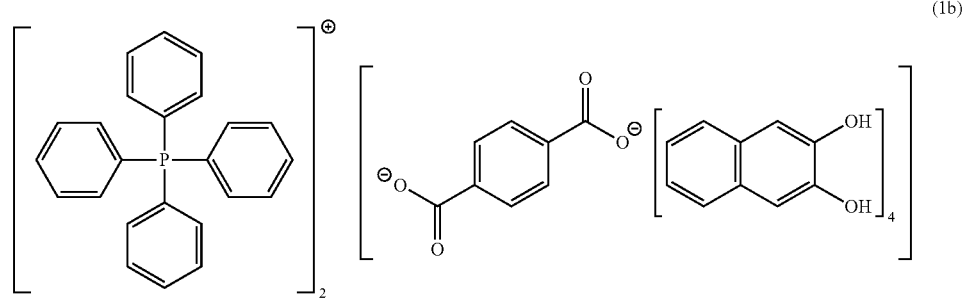

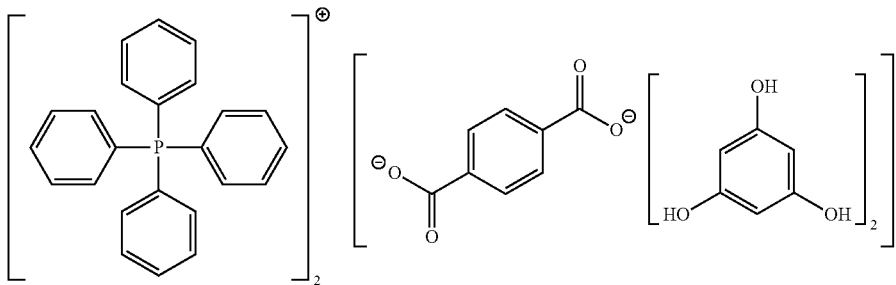
(1c)
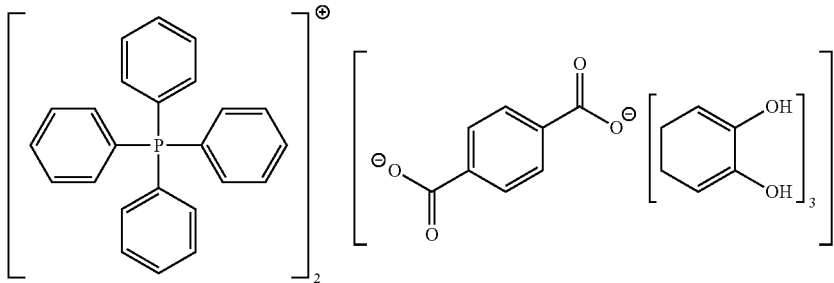
(1d)
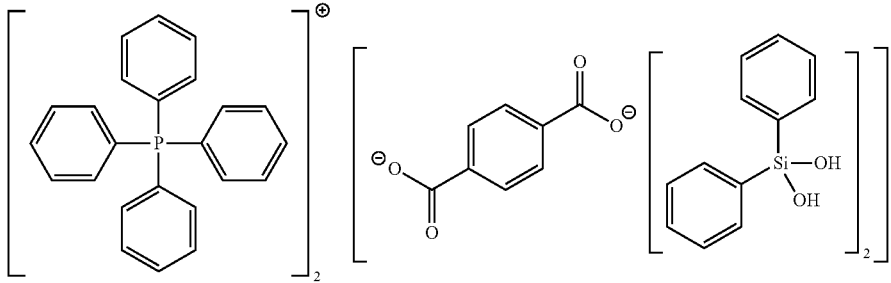
(1e)
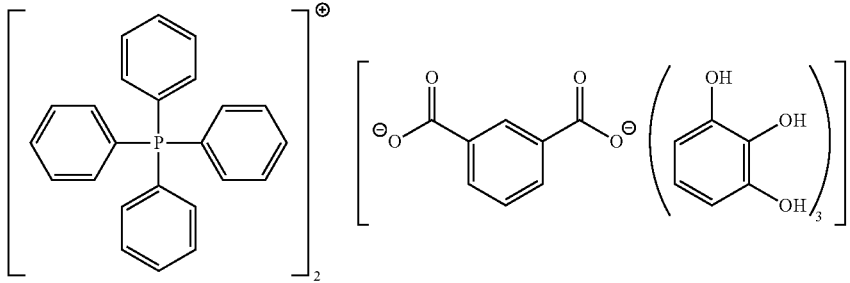
(1f)
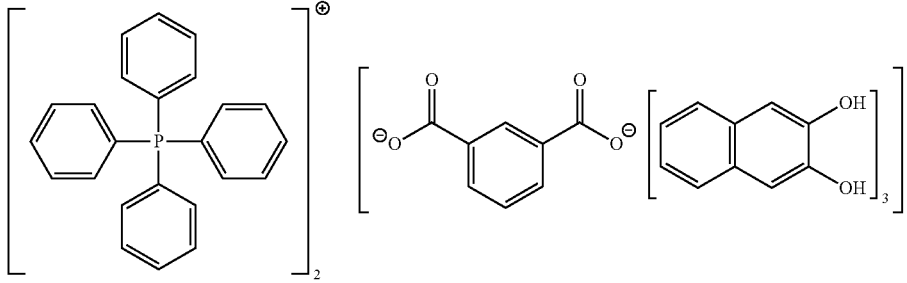
(1g)

-continued

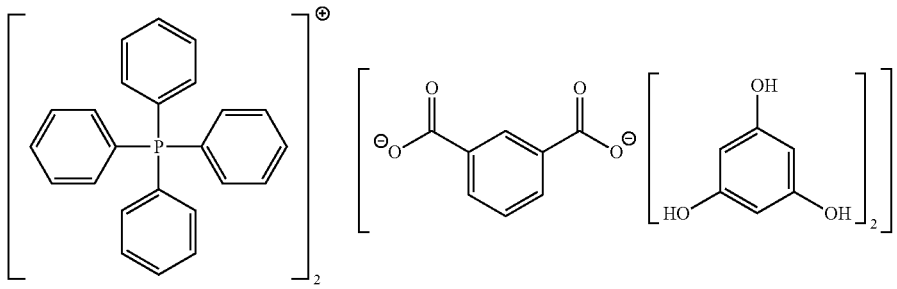

(1h)

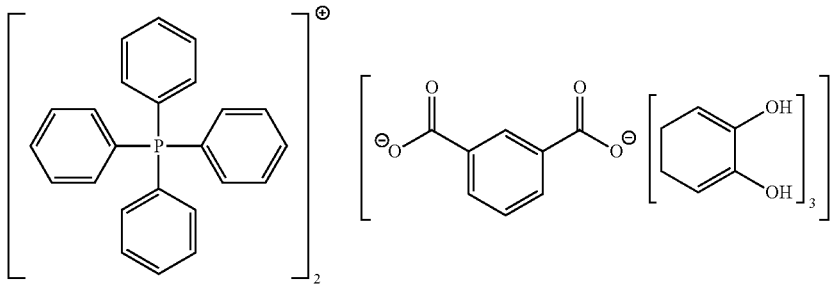

(1i)

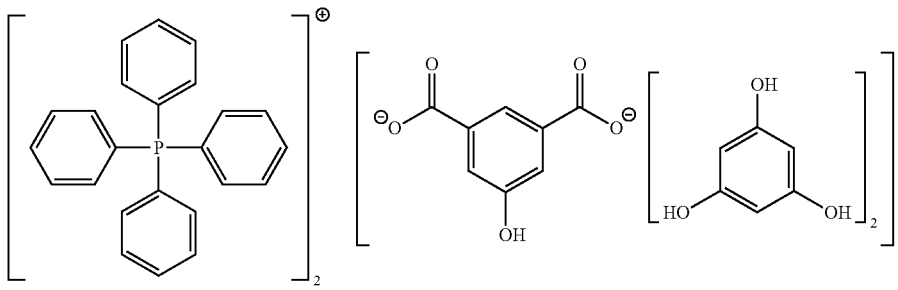

(1j)

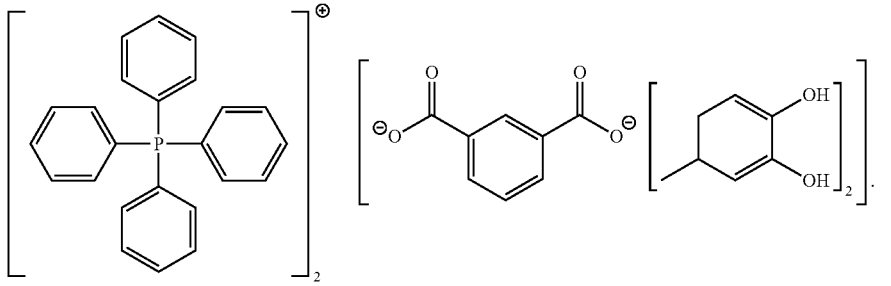

(1k)

The embodiments may be realized by providing an epoxy resin composition including an epoxy resin, a curing agent, a curing accelerator, and an inorganic filler, wherein the curing accelerator includes a quaternary phosphonium salt represented by Formula 1:

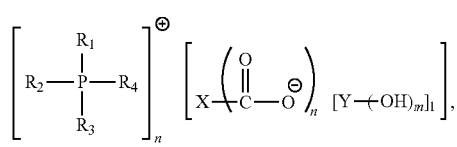

(1)

wherein, in Formula 1 $R_1$, $R_2$, $R_3$, and $R_4$ are each independently a substituted or unsubstituted $C_1$-$C_{30}$ hydrocarbon group or a substituted or unsubstituted $C_1$-$C_{30}$ hydrocarbon group including at least one heteroatom; X is a substituted or unsubstituted $C_1$-$C_{30}$ hydrocarbon group or a substituted or unsubstituted $C_1$-$C_{30}$ hydrocarbon group including at least one heteroatom; Y is a substituted or unsubstituted $C_1$-$C_{30}$ hydrocarbon group or Si substituted with one to three substituted or unsubstituted $C_1$-$C_{30}$ hydrocarbon groups; n and m are each independently an integer from 1 to 6, provided that when Y is Si, a sum of m and a number of substituents on the Si is a maximum of 4; and l is a number greater than 0 and up to 6.

$R_1$, $R_2$, $R_3$, and $R_4$ may each independently be a substituted or unsubstituted benzene group.

X may be a substituted or unsubstituted benzene group.

Y may be a substituted or unsubstituted benzene group, a substituted or unsubstituted naphthalene group, or Si substituted with one to three substituted or unsubstituted benzene groups.

n may be 2.

m may be 2 or 3.

l may be 2, 3, or 4.

The quaternary phosphonium salt may be represented by one of Formulae 1a to 1k:
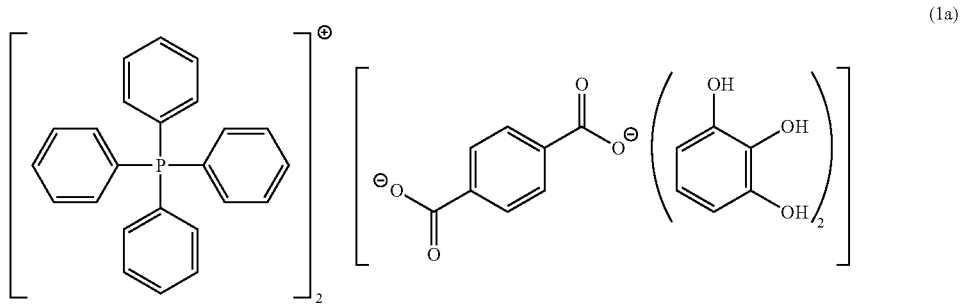
(1a)
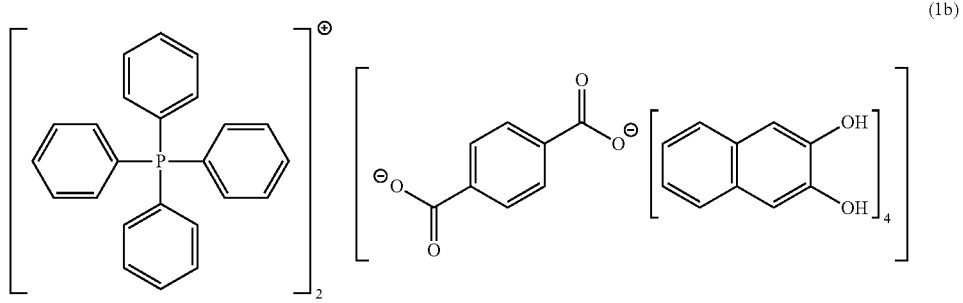
(1b)
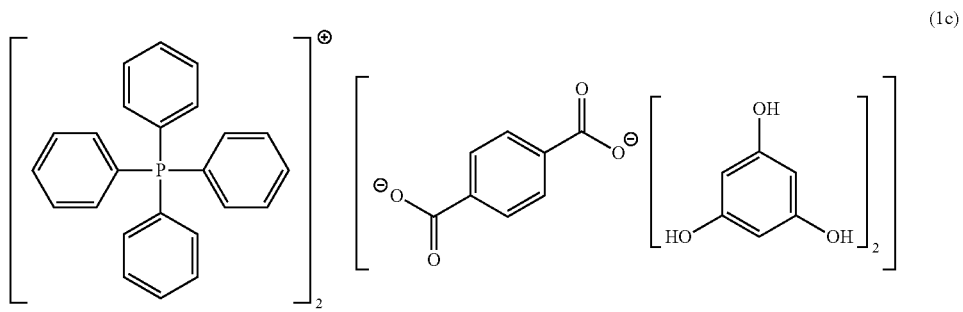
(1c)
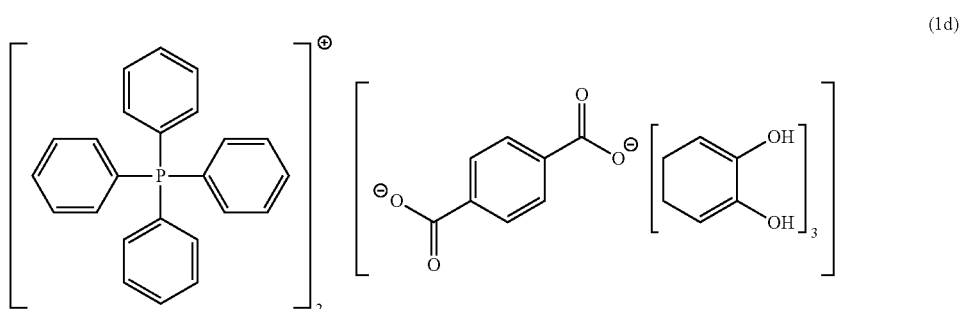
(1d)
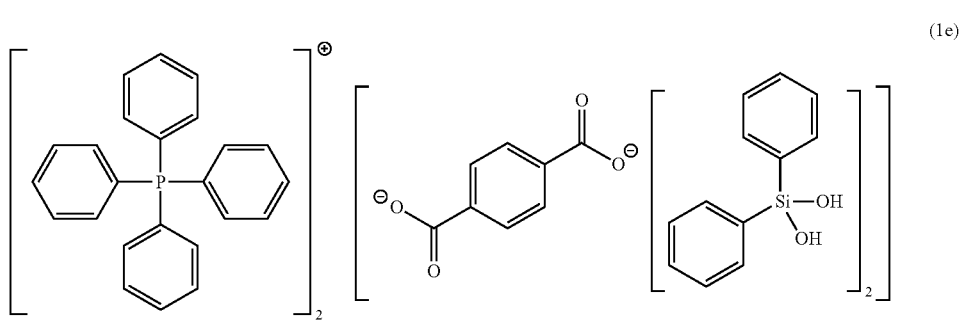
(1e)

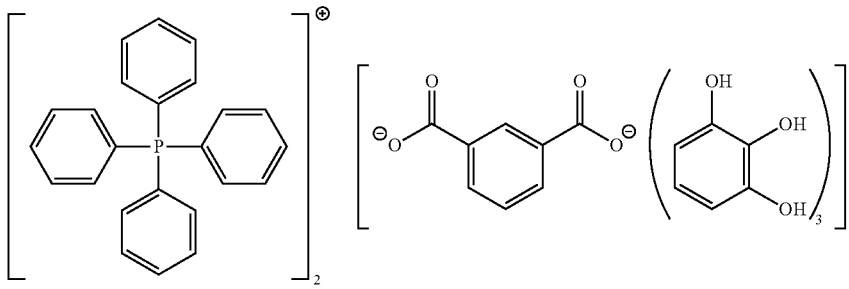
(1f)
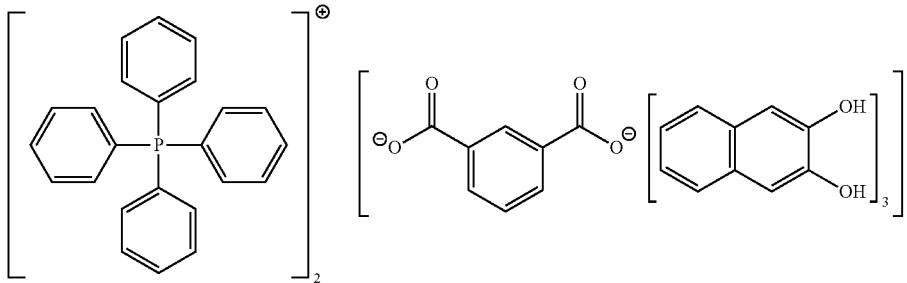
(1g)
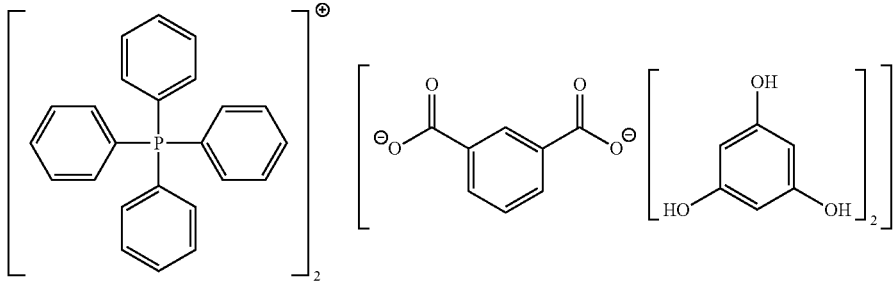
(1h)
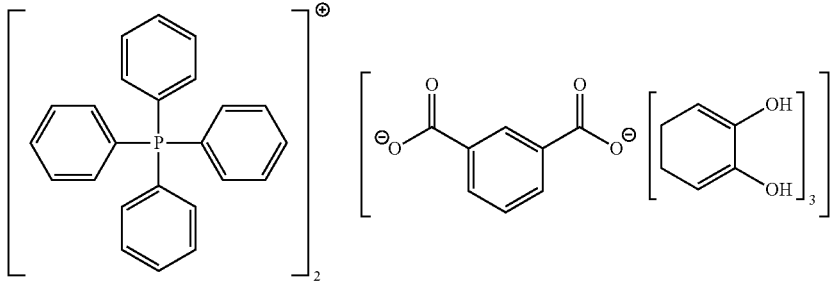
(1i)
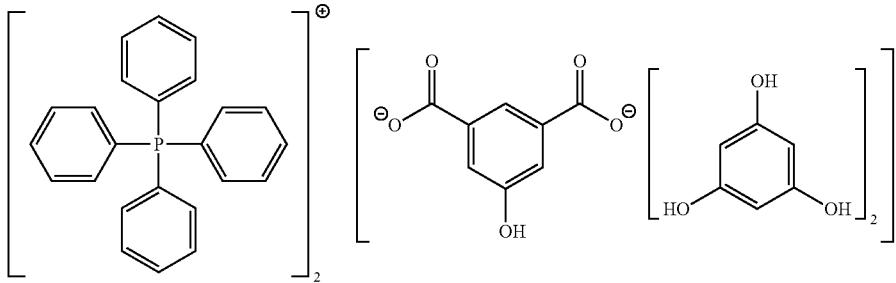
(1j)

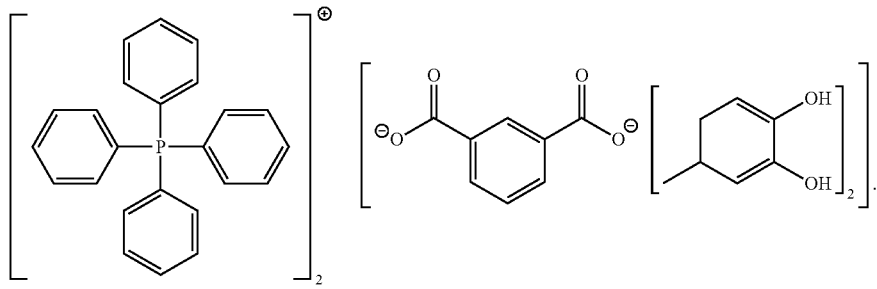

(1k)

The epoxy resin composition may include about 1% to about 20% by weight of the epoxy resin, about 1% to about 20% by weight of the curing agent, about 0.001% to about 2% by weight of the curing accelerator, and about 70% to about 95% by weight of the inorganic filler.

The epoxy resin may include at least one of an epoxy resin obtained by epoxidation of condensation products of phenol or alkyl phenols and hydroxybenzaldehyde, a phenol novolac type epoxy resin, a cresol novolac type epoxy resin, a polyfunctional epoxy resin, a naphthol novolac type epoxy resin, a novolac type epoxy resin of bisphenol A/bisphenol F/bisphenol AD, a glycidyl ether of bisphenol A/bisphenol F/bisphenol AD, a bishydroxybiphenyl-based epoxy resin, a dicyclopentadiene-based epoxy resin, a biphenyl type epoxy resin, a polycyclic aromatic-modified epoxy resin, a bisphenol A type epoxy resin, an ortho-cresol novolac type epoxy resin, a phenol aralkyl type epoxy resin, or a naphthalene-based epoxy resin.

The curing agent may include at least one of a phenol aralkyl type phenolic resin, a xyloc type phenolic resin, a phenol novolac type phenolic resin, a cresol novolac type phenolic resin, a naphthol type phenolic resin, a terpene type phenolic resin, a polyfunctional phenolic resin, a polycyclic aromatic phenolic resin, a dicyclopentadiene-based phenolic resin, a terpene-modified phenolic resin, a dicyclopentadiene-modified phenolic resin, a novolac type phenolic resin synthesized from bisphenol A and resorcinol, a polyhydric phenolic compound, an acid anhydride, a metaphenylenediamine, a diaminodiphenylmethane, or a diaminodiphenylsulfone.

The epoxy resin and the curing agent may be present in amounts such that a ratio of an epoxy equivalent weight of the epoxy resin to a phenolic hydroxyl equivalent weight or an amine equivalent weight of the curing agent is about 0.5:1 to about 2:1.

The inorganic filler may include at least one of fused silica, crystalline silica, calcium carbonate, magnesium carbonate, alumina, magnesia, clay, talc, calcium silicate, titanium oxide, antimony oxide, or glass fiber.

The epoxy resin composition may further include at least one of a colorant, a coupling agent, a release agent, a stress-relieving agent, a cross-linking enhancer, a leveling agent, or a flame retardant.

The embodiments may be realized by providing a semiconductor device encapsulated with the epoxy resin composition according to an embodiment.

BRIEF DESCRIPTION OF THE DRAWING

Features will be apparent to those of skill in the art by describing in detail exemplary embodiments with reference to the attached drawing in which:

FIG. 1 illustrates a semiconductor device encapsulated with an epoxy resin composition according to an embodiment.

DETAILED DESCRIPTION

Embodiments will now be described in detail.

An embodiment provides a quaternary phosphonium salt represented by Formula 1, below.

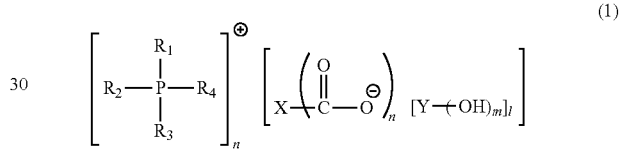

In Formula 1, $R_1$, $R_2$, $R_3$, and $R_4$ may each independently be a substituted or unsubstituted $C_1$-$C_{30}$ hydrocarbon group (e.g., a $C_1$-$C_{12}$ hydrocarbon group) or a substituted or unsubstituted $C_1$-$C_{30}$ hydrocarbon group including at least one heteroatom. For example, $R_1$, $R_2$, $R_3$, and $R_4$ may each independently be a $C_1$-$C_{12}$ hydrocarbon group or a substituted or unsubstituted benzene group. X may be a substituted or unsubstituted $C_1$-$C_{30}$ hydrocarbon group or a substituted or unsubstituted $C_1$-$C_{30}$ hydrocarbon group including at least one heteroatom. For example, X may be a $C_1$-$C_{12}$ hydrocarbon group or a $C_1$-$C_{12}$ hydrocarbon group or a substituted or unsubstituted benzene group. Y may be a substituted or unsubstituted $C_1$-$C_{30}$ hydrocarbon group or Si substituted with one to three substituted or unsubstituted $C_1$-$C_{30}$ hydrocarbon groups. For example, Y may be a $C_1$-$C_{12}$ hydrocarbon group or $C_1$-$C_{12}$ hydrocarbon groups, a substituted or unsubstituted benzene group, a substituted or unsubstituted naphthalene group, or Si substituted with one to three substituted or unsubstituted benzene groups. n and m may each independently be an integer from 1 to 6, e.g., n may be 2 and/or m may be 2 or 3. l may be a number greater than 0 and up to 6, e.g., 2, 3, or 4. In an implementation, when Y is Si, a sum of m and a number of substituents (on the Si) may be a maximum of 4.

The term "substituted" used herein may mean that at least one hydrogen atom is substituted with a halogen atom, a hydroxyl group, a $C_1$-$C_{10}$ alkyl group, a $C_1$-$C_{10}$ haloalkyl group, a $C_6$-$C_{10}$ aryl group, a $C_1$-$C_{10}$ alkoxy group, or a combination thereof. The term "heteroatom" means the presence of at least one atom of oxygen (O), sulfur (S), and nitrogen (N) atoms.

There is no restriction on the method of preparing the quaternary phosphonium salt. For example, the quaternary phosphonium salt may be prepared by dissolving a carboxylic acid compound (corresponding to the carboxylate anion moiety of Formula 1) in a basic solution, e.g., an aqueous sodium hydroxide (NaOH) solution, adding a solution of a hydroxyl compound (corresponding to the hydroxyl moiety of Formula 1) and a halogenated quaternary phosphonium (corresponding to the quaternary phosphonium cation moiety of Formula 1) in an alcohol such as methanol, allowing the mixture to react for about 1 hour, and drying the resulting precipitate. For example, a method of preparing the quaternary phosphonium salt will be described in greater detail below in the examples.

In an implementation, the quaternary phosphonium salt may be represented by one of Formulae 1a to 1k:

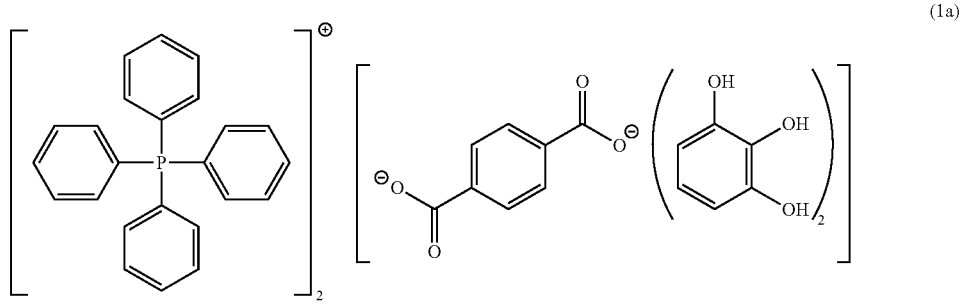

(1a)

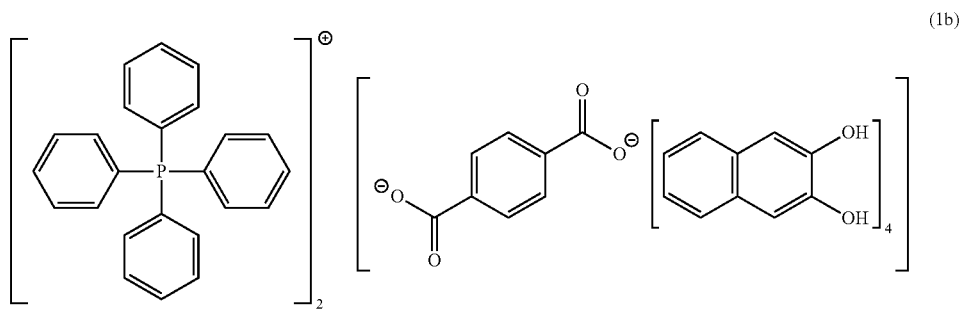

(1b)

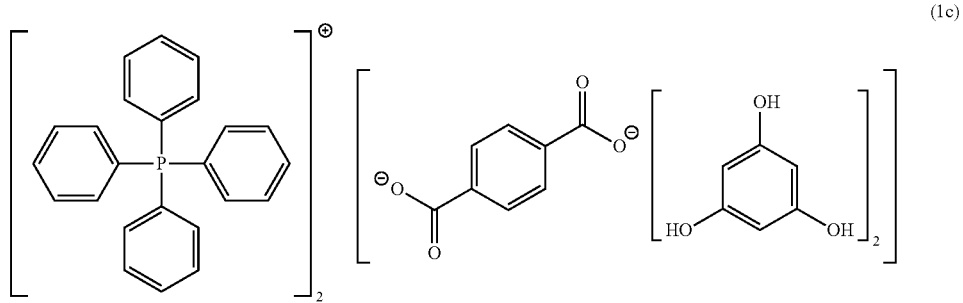

(1c)

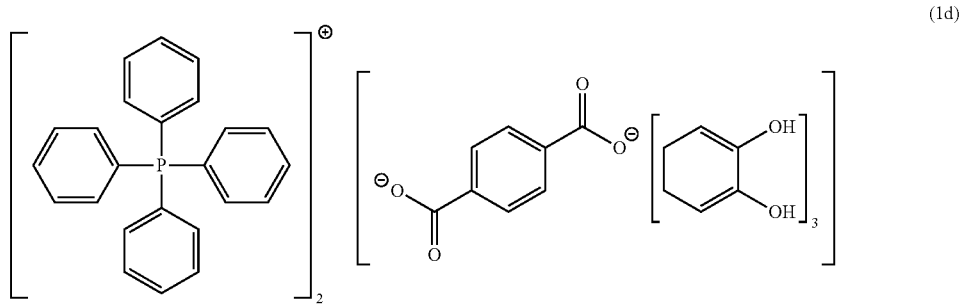

(1d)

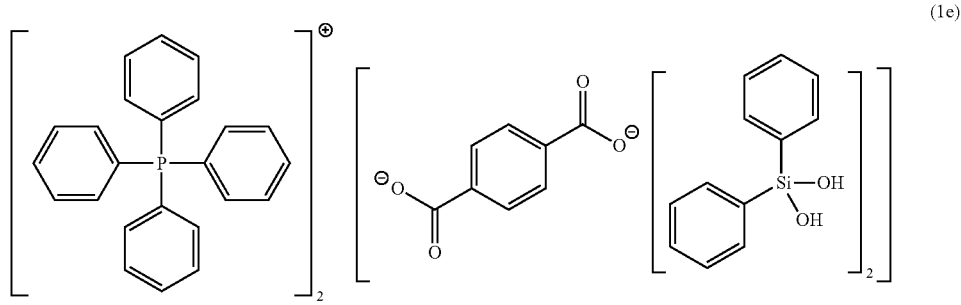
(1e)
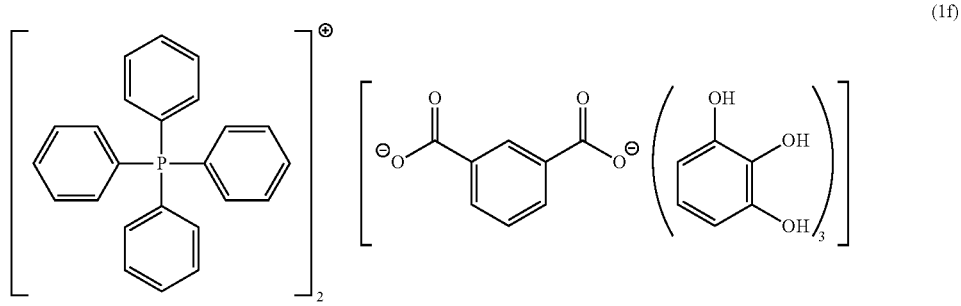
(1f)
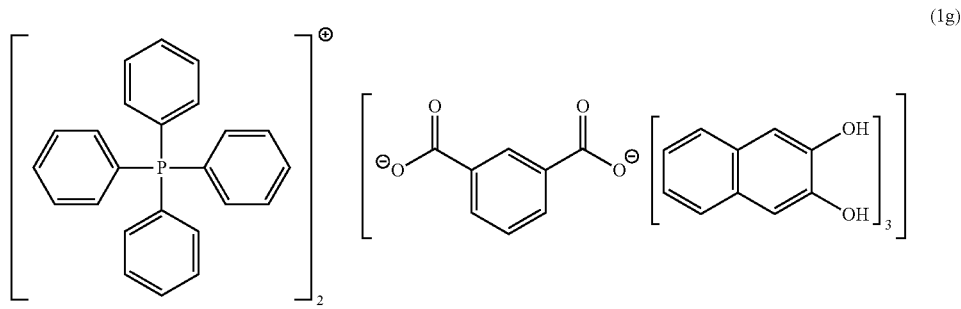
(1g)
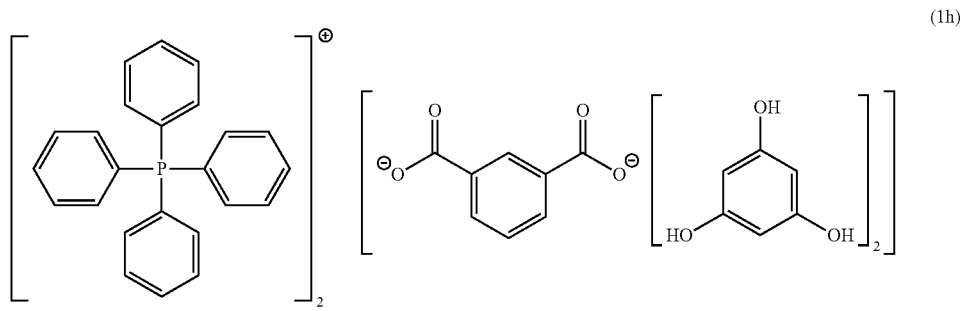
(1h)
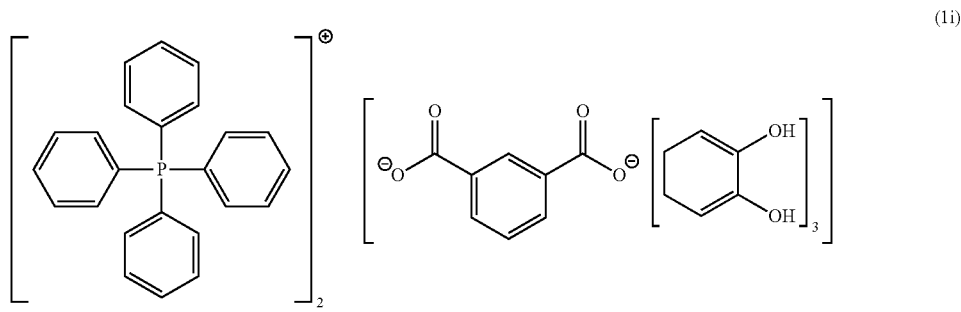
(1i)

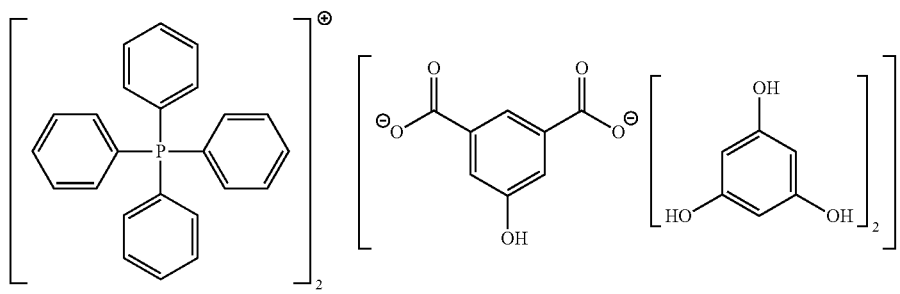

(1j)

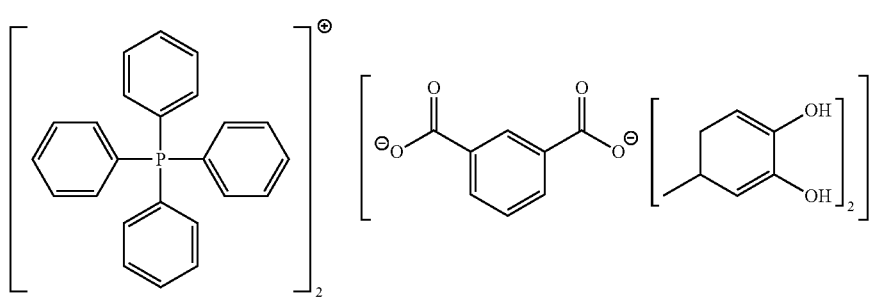

(1k)

Another embodiment provides an epoxy resin composition. The epoxy resin composition may include, e.g., an epoxy resin, a curing agent, a curing accelerator, and an inorganic filler. The epoxy resin composition may be useful in encapsulating a semiconductor device.

Epoxy Resin

The epoxy resin may be a suitable epoxy resin for an epoxy resin composition for encapsulating semiconductor devices. A suitable epoxy resin having two or more epoxy groups in the molecule may be used without particular limitation. For example, the epoxy resin may include an epoxy monomer, an epoxy oligomer, an epoxy polymer, or a combination thereof.

Specific examples of epoxy resins suitable for use in the embodiments may include epoxy resins obtained by epoxidation of condensation products of phenol or alkyl phenols and hydroxybenzaldehyde, phenol novolac type epoxy resins, cresol novolac type epoxy resins, polyfunctional epoxy resins, naphthol novolac type epoxy resins, novolac type epoxy resins of bisphenol A/bisphenol F/bisphenol AD, glycidyl ethers of bisphenol A/bisphenol F/bisphenol AD, bishydroxybiphenyl-based epoxy resins, dicyclopentadiene-based epoxy resins, biphenyl type epoxy resins, polycyclic aromatic-modified epoxy resins, bisphenol A type epoxy resins, ortho-cresol novolac type epoxy resins, phenol aralkyl type epoxy resins, and naphthalene-based epoxy resins. The epoxy resins may be used alone or in combination of two or more thereof.

The epoxy resin may impart excellent mechanical properties to the epoxy resin composition. In an implementation, the epoxy resin may include a phenol aralkyl type epoxy resin having a novolac structure including at least one biphenyl moiety in the molecule, as represented by Formula 2, below

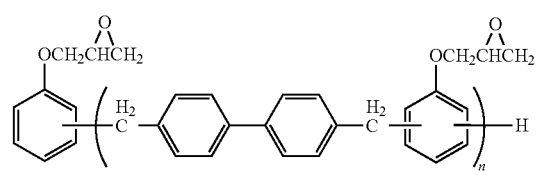

(2)

In Formula 2, n may be an average of 1 to 7.

In an implementation, the epoxy resin may include a biphenyl type epoxy resin represented by Formula 3, below.

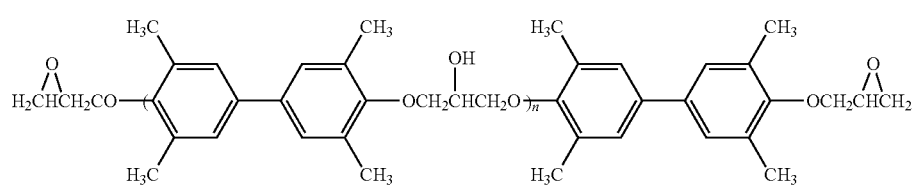

(3)

In Formula 3, n may be an average of 0 to 7.

In an implementation, the epoxy resin may include a xyloc type epoxy resin represented by Formula 4, below.

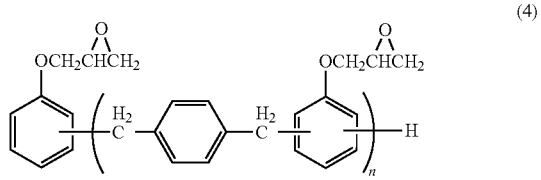

(4)

In Formula 4, n may be an average of 1 to 7.

In an implementation, the epoxy resin may include a polyfunctional epoxy resin including naphthalene skeletons, represented by Formula 5, below.

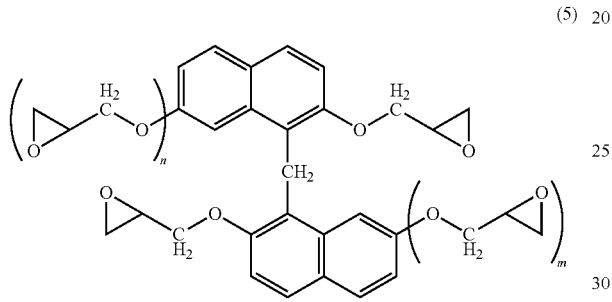

(5)

In Formula 5, m and n may each independently be an average of 0 to 6.

The epoxy resins may be used alone or in combination.

In an implementation, the epoxy resin may also be used in the form of an adduct, e.g., a melt master batch obtained by pre-reacting with the curing agent, the curing accelerator, and optionally one or more additives such as a release agent or a coupling agent.

The epoxy resin may be present in the composition in an amount of about 1% to about 20% by weight, e.g., about 1% to about 13% by weight or about 1.2% to about 10% by weight, based on a total weight of the epoxy resin composition. Within this range, good room temperature storage stability, sufficient flowability, and high curability of the epoxy resin composition may be ensured.

Curing Agent

The curing agent may be a suitable curing agent used for the encapsulation of semiconductor devices. In an implementation, the curing agent may have two or more phenolic hydroxyl or amino groups. The curing agent may be, e.g., a monomer, an oligomer, a polymer, or a combination thereof.

Specific examples of curing agents suitable for use in the embodiments may include phenol aralkyl type phenolic resins, xyloc type phenolic resins, phenol novolac type phenolic resins, cresol novolac type phenolic resin, naphthol type phenolic resins, terpene type phenolic resins, polyfunctional phenolic resins, polycyclic aromatic phenolic resins, dicyclopentadiene-based phenolic resins, terpene-modified phenolic resins, dicyclopentadiene-modified phenolic resin, novolac type phenolic resins synthesized from bisphenol A and resorcinol, polyhydric phenolic compounds (e.g., including tris(hydroxyphenyl)methane and dihydroxybiphenyl), acid anhydrides (e.g., including maleic anhydride and phthalic anhydride), and aromatic amines (e.g., including metaphenylenediamine, diaminodiphenylmethane and diaminodiphenylsulfone).

In an implementation, the curing agent may be a phenol aralkyl type phenolic resin having at least one biphenyl skeleton (as represented by Formula 6, below) a xyloc type phenolic resin (represented by Formula 7, below), or combinations thereof.

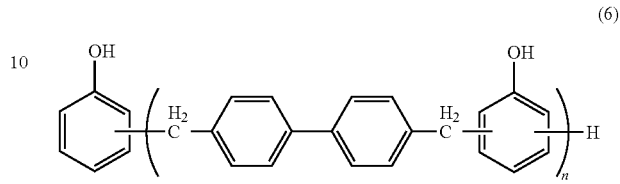

(6)

In Formula 6, n may be an average of about 1 to about 7.

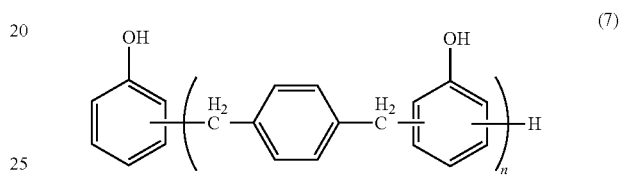

(7)

In Formula 7, n may be an average of about 1 to about 7.

In an implementation, the curing agents may be used alone or in combination with one or two other components. For example, the curing agent may be used in the form of an adduct, such as a melt master batch obtained by pre-reacting with the epoxy resin, the curing accelerator, and other additives.

The curing agent may have a softening point of about 50° C. to about 100° C., e.g., about 60° C. to about 90° C. Within this range, the viscosity of the resin composition may be appropriate so that deterioration of the flowability of the resin composition may be prevented.

A phenolic hydroxyl equivalent weight or amine equivalent weight of the curing agent may be from about 90 g/eq to about 300 g/eq, but is not limited to this range.

The curing agent may be present in the composition in an amount of about 1% to about 20% by weight, e.g., about 1.5% to about 10% by weight or about 2% to about 8% by weight, based on the total weight of the epoxy resin composition. Within this range, appreciable amounts of the epoxy groups and phenolic hydroxyl or amino groups may not remain unreacted, thereby ensuring high reliability of the epoxy resin composition.

In an implementation, the epoxy resin and the curing agent may be present in amounts such that a ratio of the epoxy equivalent weight of the epoxy resin to the phenolic hydroxyl equivalent weight or amine equivalent weight of the curing agent is about 0.5:1 to about 2:1, e.g., about 0.8:1 to about 1.6:1. Within this range, sufficient flowability of the resin composition may be ensured, and curing time may not be needlessly extended.

Curing Accelerator

The curing accelerator may help promote a reaction between the epoxy resin and the curing agent. The curing accelerator may include the quaternary phosphonium salt represented by Formula 1.

The curing accelerator represented by Formula 1 may be in the form of a salt of a quaternary phosphonium. The curing accelerator may be highly stable during storage at room temperature (~25° C.) and a humidity of 50%, and may be sufficiently flowable during molding. When a curing reaction occurs, a hydrogen bond between the carboxylic acid anion and the (phenolic) hydroxyl group derived from different molecules may be rapidly cleaved. This bond cleavage may cause a significant increase in the degree of freedom of the phosphonium cation as a catalytic moiety, thereby facilitating fast curing and helping to provide excellent curing properties, e.g., high cure strength.

The curing accelerator may be combined with one or more other curing accelerators. The other curing accelerators may include, e.g., tertiary amines, organometallic compounds, organophosphorous compounds, imidazole compounds, or boron compounds. The curing accelerator may also be used in the form of an adduct obtained by pre-reacting with the epoxy resin and/or the curing agent.

The curing accelerator may be present in the composition in an amount of about 0.001% to about 2% by weight, e.g., about 0.001% to about 1.5% by weight or about 0.01% to about 1% by weight, based on the total weight of the epoxy resin composition. Within this range, good room temperature storage stability of the epoxy resin composition may be obtained, curing time may not be needlessly extended, and sufficient flowability of the composition may be provided.

Inorganic Filler

The inorganic filler may help improve the mechanical properties of the epoxy resin composition and may help reduce stress in the epoxy resin composition. The inorganic filler may include a suitable inorganic used in epoxy resin compositions for encapsulating semiconductor devices. Specific examples of inorganic fillers suitable for use in the embodiments may include fused silica, crystalline silica, calcium carbonate, magnesium carbonate, alumina, magnesia, clay, talc, calcium silicate, titanium oxide, antimony oxide, and glass fiber. The inorganic fillers may be used alone or as a mixture of two or more thereof.

Fused silica (having a low coefficient of linear expansion) may be desirable in terms of stress reduction. The fused silica may refer to amorphous silica having a specific gravity not higher than about 2.3. The fused silica may be prepared by melting crystalline silica or may include amorphous silica products synthesized from various raw materials.

A shape and a particle diameter of the inorganic filler are not particularly limited. For example, an average particle diameter of the inorganic filler may be about 0.001 µm to about 30 µm. In an implementation, the inorganic filler may include spherical fused silica having an average particle diameter of about 0.001 µm to about 30 µm. The inorganic filler may also include a mixture of spherical fused silica products having different particle diameters. For example, the inorganic filler may include a mixture of about 50% to about 99% by weight of spherical fused silica having an average particle diameter of about 5 µm to about 30 µm and about 1% to about 50% by weight of spherical fused silica having an average particle diameter of about 0.001 µm to about 1 µm. In an implementation, the particle diameter of the inorganic filler may be adjusted to a maximum of about 45 µm, about 55 µm, or about 75 µm, depending on the application of the epoxy resin composition.

Before use, the inorganic filler may be surface treated with at least one coupling agent. The coupling agent may include, e.g., epoxysilanes, aminosilanes, mercaptosilanes, alkylsilanes, or alkoxysilanes.

The inorganic filler may be included in the composition in a suitable amount, depending on desired physical properties of the epoxy resin composition, e.g., moldability, low-stress properties, and/or high-temperature strength. In an implementation, the inorganic filler may be present in an amount of about 70% to about 95% by weight, e.g., about 75% to about 94% by weight or about 82% to about 92% by weight, based on the total weight of the epoxy resin composition. Within this range, good resistance to warpage, good flowability, and good moldability of the epoxy resin composition may be obtained, and high reliability of a package may be expected.

Additives

In an implementation, the epoxy resin composition may further include one or more additives. The additives may include, e.g., colorants, coupling agents, release agents, stress-relieving agents, cross-linking enhancers, leveling agents, flame retardants, or the like.

Examples of the colorants may include carbon black, organic dyes, and inorganic dyes.

The coupling agents may include, e.g., silane coupling agents. Examples of the silane coupling agents may include epoxysilanes, aminosilanes, mercaptosilanes, alkylsilanes, and alkoxysilanes.

Examples of the release agents may include paraffin-based waxes, ester-based waxes, higher fatty acids, metal salts of higher fatty acids, natural fatty acids, and metal salts of natural fatty acids.

Examples of the stress-relieving agents may include modified silicone oils, silicone elastomers, silicone powders, and silicone resins.

The flame retardants may be, e.g., non-halogenated (organic and inorganic) flame retardants. Examples of the non-halogenated flame retardants may include phosphazene, zinc borate, aluminum hydroxide, and magnesium hydroxide.

The additives may be included in the composition in an amount of about 0% to about 15% by weight, e.g., about 0.1% to about 5.5% by weight, based on the total weight of the epoxy resin composition. In an implementation, the flame retardant may be included in an appropriate amount depending on the flame retardancy of the epoxy resin composition, which is determined by various factors, e.g., the content of the inorganic filler and the kind of the curing agent. For example, the flame retardant may be included in an amount of about 0% to about 10% by weight, e.g., about 0% to about 8% by weight or about 0% to about 5% by weight, based on the total weight of the epoxy resin composition.

There is no particular restriction on the method of preparing the epoxy resin composition. For example, the epoxy resin composition may be prepared by the following procedure. First, all components of the resin composition may be homogenized using a suitable mixer, e.g., a Henschel mixer or a Redige mixer. Then, the mixture may be melt-kneaded in a roll mill or a kneader at 90° C. to 120° C., cooled, and pulverized.

Another embodiment provides a semiconductor device is encapsulated with the epoxy resin composition. For example, the semiconductor device may be encapsulated with the epoxy resin composition by various molding processes, e.g., low-pressure transfer molding, compression molding, injection molding, or casting molding. In an implementation, the semiconductor device may be encapsulated with the epoxy resin composition by low-pressure transfer molding. Semiconductor devices that may be encapsulated by the molding processes may include copper lead frames, iron lead frames, copper or iron lead frames pre-plated with at least one of nickel, copper and palladium, organic laminate frames, and the like.

FIG. 1 illustrates a semiconductor device encapsulated with an epoxy resin composition according to an embodiment. For example, the semiconductor device 100 encapsulated with the epoxy resin composition may include a lead frame 110 and an encapsulant 115 (prepared from the epoxy resin composition according to an embodiment) on the lead frame 110.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Preparative Example 1

Preparation of Quaternary Phosphonium Salt Represented by Formula 1a 19.8 g of terephthalic acid was dissolved in 237 mL of a 1 M aqueous NaOH solution. To the solution was slowly added a solution of 30.1 g of pyrogallol and 100 g of tetraphenylphosphonium bromide in 100 mL of methanol. The mixture was allowed to react for 1 h. The resulting precipitate was filtered and dried to afford 106 g of the quaternary phosphonium salt represented by Formula 1a as a pale brown solid.

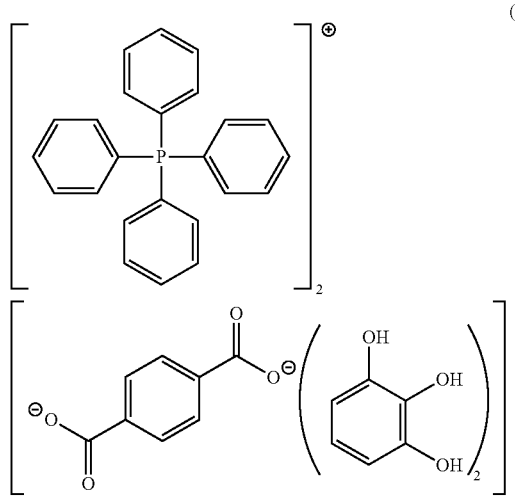

Preparative Example 2

Preparation of Quaternary Phosphonium Salt Represented by Formula 1b 19.8 g of terephthalic acid was dissolved in 237 mL of a 1 M aqueous NaOH solution. To the solution was slowly added a solution of 76.4 g of 2,3-dihydroxynaphthalene and 100 g of tetraphenylphosphonium bromide in 100 mL of methanol. The mixture was allowed to react for 1 h. The resulting precipitate was filtered and dried to afford 152 g of the quaternary phosphonium salt represented by Formula 1b as a pale brown solid.

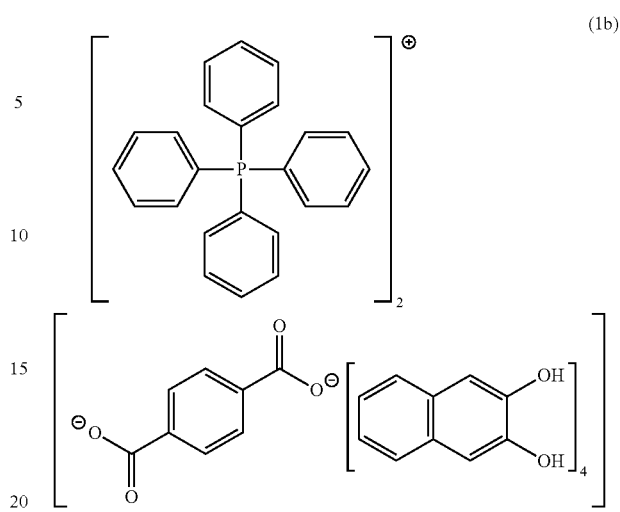

Preparative Example 3

Preparation of Quaternary Phosphonium Salt Represented by Formula 1c 19.8 g of terephthalic acid was dissolved in 237 mL of a 1 M aqueous NaOH solution. To the solution was slowly added a solution of 30.1 g of phloroglucinol and 100 g of tetraphenylphosphonium bromide in 100 mL of methanol. The mixture was allowed to react for 1 h. The resulting precipitate was filtered and dried to afford 148 g of the quaternary phosphonium salt represented by Formula 1c as a pale brown solid.

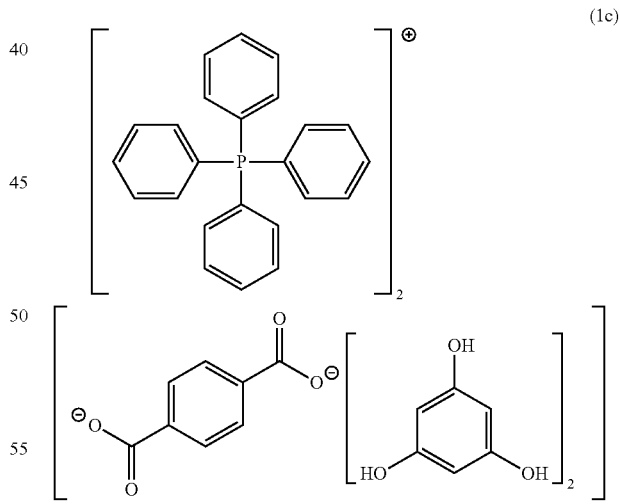

Preparative Example 4

Preparation of Quaternary Phosphonium Salt Represented by Formula 1d 19.8 g of terephthalic acid was dissolved in 237 mL of a 1 M aqueous NaOH solution. To the solution was slowly added a solution of 39.3 g of catechol and 100 g of tetraphenylphosphonium bromide in 100 mL of methanol. The mixture was allowed to react for 1 h. The resulting precipitate was filtered and dried to afford 115 g of the quaternary phosphonium salt represented by Formula 1d as a pale brown solid.

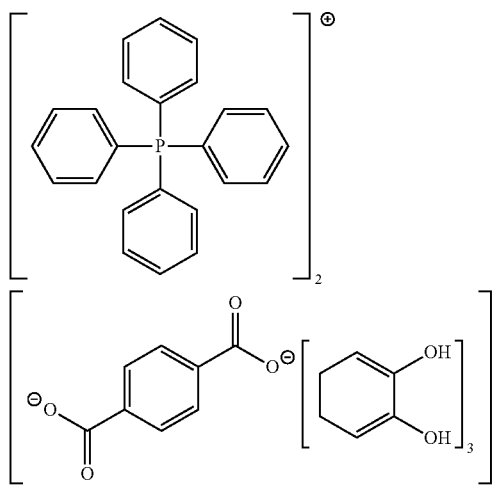

(1d)

Preparative Example 5

Preparation of Quaternary Phosphonium Salt Represented by Formula 1e 19.8 g of terephthalic acid was dissolved in 237 mL of a 1 M aqueous NaOH solution. To the solution was slowly added a solution of 53.2 g of diphenylsilanediol and 100 g of tetraphenylphosphonium bromide in 100 mL of methanol. The mixture was allowed to react for 1 h. The resulting precipitate was filtered and dried to afford 146 g of the quaternary phosphonium salt represented by Formula 1e as a pale brown solid.

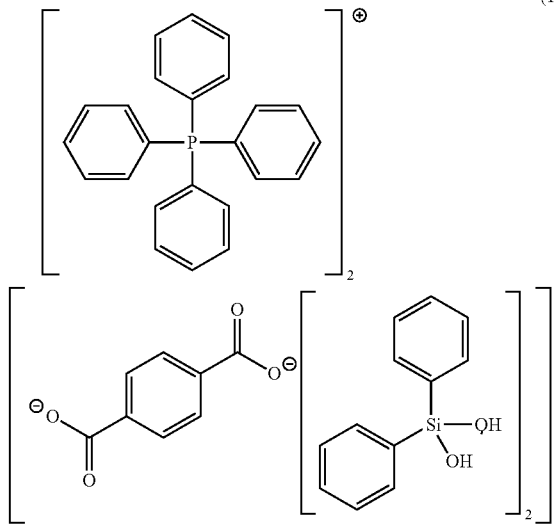

(1e)

Preparative Example 6

Preparation of Quaternary Phosphonium Salt Represented by Formula 1f 19.8 g of isophthalic acid was dissolved in 237 mL of a 1 M aqueous NaOH solution. To the solution was slowly added a solution of 45.2 g of pyrogallol and 100 g of tetraphenylphosphonium bromide in 100 mL of methanol. The mixture was allowed to react for 1 h. The resulting precipitate was filtered and dried to afford 116 g of the quaternary phosphonium salt represented by Formula 1f as a pale brown solid.

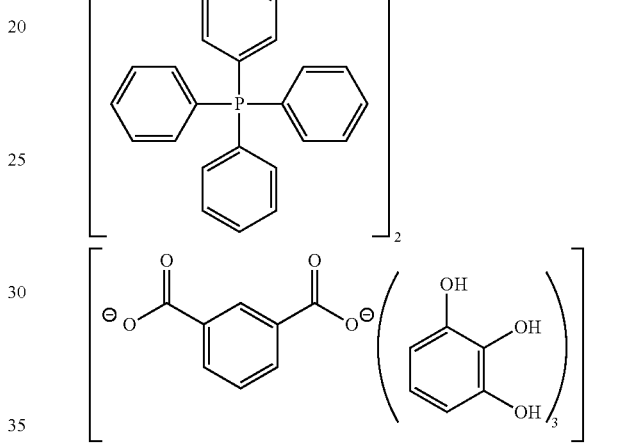

(1f)

Preparative Example 7

Preparation of Quaternary Phosphonium Salt Represented by Formula 1g 19.8 g of isophthalic acid was dissolved in 237 mL of a 1 M aqueous NaOH solution. To the solution was slowly added a solution of 57.3 g of 2,3-dihydroxynaphthalene and 100 g of tetraphenylphosphonium bromide in 100 mL of methanol. The mixture was allowed to react for 1 h. The resulting precipitate was filtered and dried to afford 122 g of the quaternary phosphonium salt represented by Formula 1g as a pale brown solid.

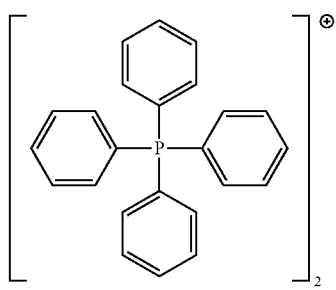

(1g)

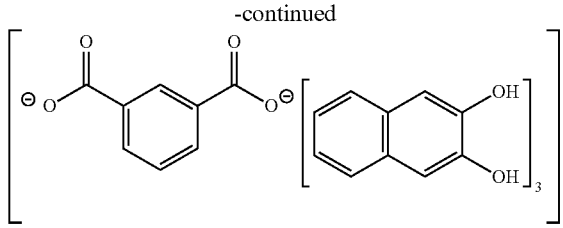

Preparative Example 8

Preparation of Quaternary Phosphonium Salt Represented by Formula 1h 19.8 g of isophthalic acid was dissolved in 237 mL of a 1 M aqueous NaOH solution. To the solution was slowly added a solution of 60.2 g of phloroglucinol and 100 g of tetraphenylphosphonium bromide in 100 mL of methanol. The mixture was allowed to react for 1 h. The resulting precipitate was filtered and dried to afford 108 g of the quaternary phosphonium salt represented by Formula 1h as a pale brown solid.

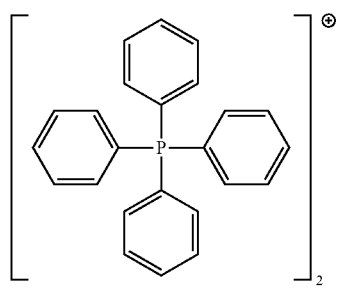

Preparative Example 9

Preparation of Quaternary Phosphonium Salt Represented by Formula 1i 19.8 g of isophthalic acid was dissolved in 237 mL of a 1 M aqueous NaOH solution. To the solution was slowly added a solution of 39.3 g of catechol and 100 g of tetraphenylphosphonium bromide in 100 mL of methanol. The mixture was allowed to react for 1 h. The resulting precipitate was filtered and dried to afford 115 g of the quaternary phosphonium salt represented by Formula 1i as a pale brown solid.

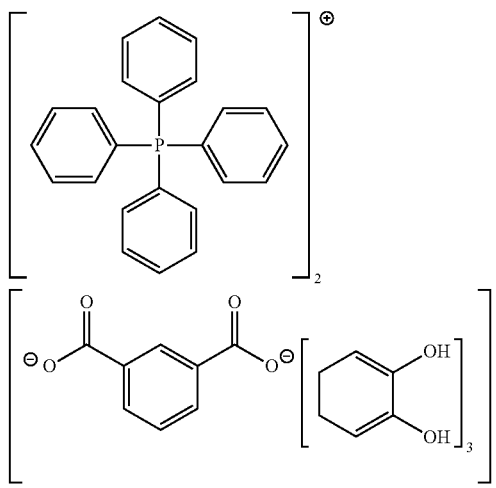

Preparative Example 10

Preparation of Quaternary Phosphonium Salt Represented by Formula 1j 21.7 g of 5-hydroxyisophthalic acid was dissolved in 237 mL of a 1 M aqueous NaOH solution. To the solution was slowly added a solution of 30.1 g of phloroglucinol and 100 g of tetraphenylphosphonium bromide in 100 mL of methanol. The mixture was allowed to react for 1 h. The resulting precipitate was filtered and dried to afford 108 g of the quaternary phosphonium salt represented by Formula 1j as a pale brown solid.

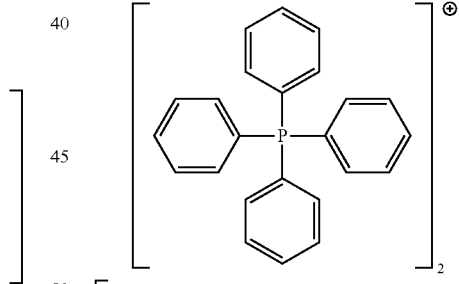

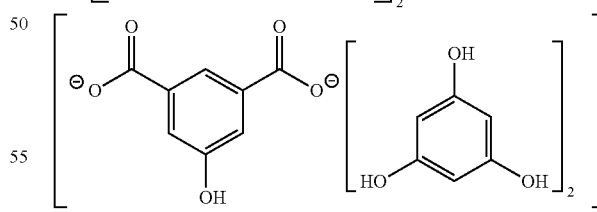

Preparative Example 11

Preparation of Quaternary Phosphonium Salt Represented by Formula 1k 19.8 g of isophthalic acid was dissolved in 237 mL of a 1 M aqueous NaOH solution. To the solution was slowly added a solution of 30.0 g of 4-methylcatechol and 100 g of tetraphenylphosphonium bromide in 100 mL of methanol. The mixture was allowed to react for 1 h. The resulting precipitate was filtered and dried to afford 101 g of the quaternary phosphonium salt represented by Formula 1k as a pale brown solid.

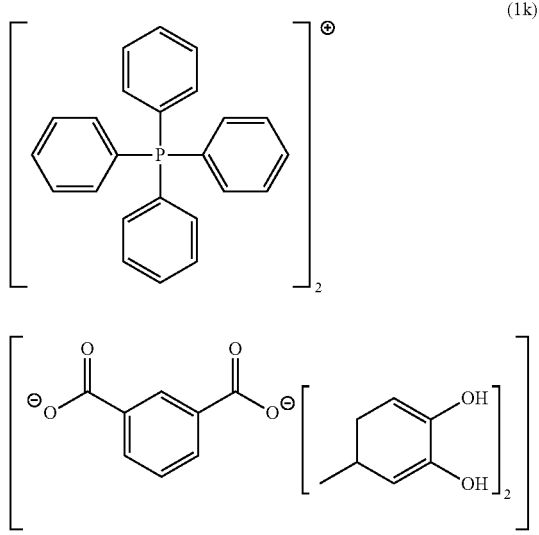

(C12): Triphenylphosphine was used.

(C13): An adduct of triphenylphosphine and 1,4-benzoquinone was used.

(D) Inorganic filler: A mixture of spherical fused silica having an average particle diameter of 18 μm and spherical fused silica having an average particle diameter of 0.5 μm in a weight ratio of 9:1 was used.

(E) Coupling agent

A mixture of (e1) mercaptopropyltrimethoxysilane (KBM-803, Shinetsu) and (e2) methyltrimethoxysilane (SZ-6070, Dow Corning Chemical) was used.

(F) Additives (f1): Carnauba wax was used as a release agent (f2): Carbon black (MA-600, Matsushita Chemical) was used as a colorant.

Examples 1-11 and Comparative Examples 1-2

The components were weighed as shown in Table 1, below, and homogenized using a Henschel mixer to prepare first powdery compositions. Then, each of the compositions was melt-kneaded using a continuous kneader at 95° C., cooled, and pulverized to prepare an epoxy resin composition for the encapsulation of a semiconductor device.

TABLE 1

|  |  | Example | | | | | | | | | | | Comparative Example | |
|---|---|---|---|---|---|---|---|---|---|---|---|---|---|---|
|  |  | 1 | 2 | 3 | 4 | 5 | 6 | 7 | 8 | 9 | 10 | 11 | 1 | 2 |
| (A) | | 8.69 | 8.69 | 8.69 | 8.69 | 8.69 | 8.69 | 8.69 | 8.69 | 8.69 | 8.69 | 8.69 | 8.69 | 8.69 |
| (B) | | 5.01 | 5.01 | 5.01 | 5.01 | 5.01 | 5.01 | 5.01 | 5.01 | 5.01 | 5.01 | 5.01 | 5.01 | 5.01 |
| (C) | C1 | 0.3 | — | — | — | — | — | — | — | — | — | — | — | — |
|  | C2 | — | 0.3 | — | — | — | — | — | — | — | — | — | — | — |
|  | C3 | — | — | 0.3 | — | — | — | — | — | — | — | — | — | — |
|  | C4 | — | — | — | 0.3 | — | — | — | — | — | — | — | — | — |
|  | C5 | — | — | — | — | 0.3 | — | — | — | — | — | — | — | — |
|  | C6 | — | — | — | — | — | 0.3 | — | — | — | — | — | — | — |
|  | C7 | — | — | — | — | — | — | 0.3 | — | — | — | — | — | — |
|  | C8 | — | — | — | — | — | — | — | 0.3 | — | — | — | — | — |
|  | C9 | — | — | — | — | — | — | — | — | 0.3 | — | — | — | — |
|  | C10 | — | — | — | — | — | — | — | — | — | 0.3 | — | — | — |
|  | C11 | — | — | — | — | — | — | — | — | — | — | 0.3 | — | — |
|  | C12 | — | — | — | — | — | — | — | — | — | — | — | 0.3 | — |
|  | C13 | — | — | — | — | — | — | — | — | — | — | — | — | 0.3 |
| (D) | | 85 | 85 | 85 | 85 | 85 | 85 | 85 | 85 | 85 | 85 | 85 | 85 | 85 |
| (E) | (e1) | 0.2 | 0.2 | 0.2 | 0.2 | 0.2 | 0.2 | 0.2 | 0.2 | 0.2 | 0.2 | 0.2 | 0.2 | 0.2 |
|  | (e2) | 0.2 | 0.2 | 0.2 | 0.2 | 0.2 | 0.2 | 0.2 | 0.2 | 0.2 | 0.2 | 0.2 | 0.2 | 0.2 |
| (F) | (f1) | 0.3 | 0.3 | 0.3 | 0.3 | 0.3 | 0.3 | 0.3 | 0.3 | 0.3 | 0.3 | 0.3 | 0.3 | 0.3 |
|  | (f2) | 0.3 | 0.3 | 0.3 | 0.3 | 0.3 | 0.3 | 0.3 | 0.3 | 0.3 | 0.3 | 0.3 | 0.3 | 0.3 |

Details of components used in Examples 1 to 11 and Comparative Examples 1 and 2 are as follows:

(A) Epoxy resin

A phenol aralkyl type epoxy resin (NC-3000, Nippon Kayaku) was used.

(B) Curing agent

A xyloc type phenolic resin (HE100C-10, Air Water) was used.

(C) Curing accelerators (C1)-(C11): The quaternary phosphonium salts prepared in Preparative Examples 1-11 were used, respectively.

Methods for evaluation of physical properties (1) Flowability (inches): A flow length of each of the epoxy resin compositions was measured using a transfer molding press in a testing mold at 175° C. and 70 kgf/cm$^2$ in accordance with EMMI-1-66. A higher measured value indicated better flowability.

(2) Curing shrinkage (%): Each of the epoxy resin compositions was molded using a transfer molding press in an ASTM mold for flexural strength specimen construction at 175° C. and 70 kgf/cm$^2$ to obtain a molded specimen (125×12.6×6.4 mm). The specimen was subjected to post-molding cure (PMC) in an oven at 170-180° C. for 4 h. After cooling, a length of the specimen was measured using calipers. The curing shrinkage of the epoxy resin composition was calculated by Equation 1:

$$\text{Curing Shrinkage} = (\text{Length of the mold at } 175° \text{C.} - \text{Length of the specimen}) \div (\text{Length of the mold at } 175° \text{C.}) \times 100 \quad (1)$$

(3) Glass transition temperature (° C.) was measured using a thermomechanical analyzer (TMA) while heating at a rate of 10° C./min from 25° C. to 300° C.

(4) Moisture absorption (%): Each of the resin compositions prepared in Examples 1-11 and Comparative Examples 1-2 was molded at a mold temperature of 170-180° C., a clamp pressure of 70 kg/cm², a transfer pressure of 1,000 psi and a transfer speed of 0.5-1 cm/s for a curing time of 120 sec to obtain a cured specimen in the form of a disc having a diameter of 50 mm and a thickness of 1 mm. The specimen was subjected to post-molding cure (PMC) in an oven at 170-180° C. for 4 h and allowed to stand at 85° C. and 85 RH % for 168 h. The weights of the specimen before and after moisture absorption were measured. The moisture absorption of the resin composition was calculated by Equation 2:

$$\text{Moisture absorption}(\%) = (\text{Weight of the specimen after moisture absorption} - \text{Weight of the specimen before moisture absorption}) \div (\text{Weight of the specimen before moisture absorption}) \times 100 \quad (2)$$

(5) Adhesive strength (kgf): A copper metal device having a specification adapted to a mold for adhesive strength measurement was prepared as a test piece. Each of the resin compositions prepared in Examples 1-11 and Comparative Examples 1-2 was molded on the test piece at a mold temperature of 170-180° C., a clamp pressure of 70 kgf/cm², a transfer pressure of 1,000 psi and a transfer speed of 0.5-1 cm/s for a curing time of 120 sec to obtain a cured specimen. The specimen was subjected to post-molding cure (PMC) in an oven at 170-180° C. for 4 h. The area of the epoxy resin composition in contact with the specimen was 40±1 mm². The adhesive strength of the epoxy resin composition was measured using a universal testing machine (UTM). 12 specimens of each composition were produced. After the measurement procedure was repeated, the measured adhesive strength values were averaged.

(6) Room temperature storage stability (%): The flowability of each of the epoxy resin compositions was measured in accordance with the method described in (1). After storage at 25° C. and a humidity of 50% for 3 days, the flowability of the epoxy resin composition was again measured. The room temperature storage stability of the epoxy resin composition was calculated by substituting the flowabilities into Equation 3:

$$\text{Room temperature storage stability} = (\text{Flowability measured after storage at } 25° \text{C. and a humidity of } 50\% \text{ for 3 days}) \div (\text{Flowability measured immediately after preparation}) \times 100 \quad (3)$$

A higher value indicated better room temperature storage stability.

(7) Degree of cure (Shore-D): Each of the epoxy resin compositions was cured using a multi plunger system (MPS) equipped with a mold at 175° C. for 50 sec, 60 sec, 70 sec, 80 sec, and 90 sec to construct exposed thin quad flat packages (eTQFPs), each including a copper metal device having a width of 20 mm, a length of 20 mm and a thickness of 1 mm. Hardness values of the cured products in the packages on the mold according to the curing periods of time were directly measured using a Shore D durometer. A higher hardness value indicated better degree of cure.

(8) Reliability: The eTQFP package for the evaluation of degree of cure (curing time 90 sec) was dried at 125° C. for 24 h. After 5 cycles of thermal shock testing (1 cycle refers to a series of exposures of the package to −65° C. for 10 min, 25° C. for 10 min, and 150° C. for 10 min), the package was allowed to stand at 85° C. and 60% RH for 168 h and treated by IR reflow three times at 260° C. for 30 sec (preconditioning). After preconditioning, the occurrence of external cracks in the package was observed using an optical microscope, and the occurrence of peeling between the epoxy resin composition and a lead frame was evaluated by scanning acoustic microscopy (C-SAM) as a non-destructive testing method. External cracks of the package or peeling between the epoxy resin composition and the lead frame mean that reliability of the package cannot be guaranteed.

Physical properties of the epoxy resin compositions prepared in Examples 1-11 and Comparative Examples 1-2 were evaluated by the above methods, and the results are shown in Table 2, below.

TABLE 2

| | | | Example | | | | | | |
|---|---|---|---|---|---|---|---|---|---|
| | | | 1 | 2 | 3 | 4 | 5 | 6 | 7 |
| Basic physical properties | Flowability (inch) | | 72 | 74 | 70 | 72 | 72 | 71 | 73 |
| | Curing shrinkage (%) | | 0.35 | 0.33 | 0.35 | 0.27 | 0.30 | 0.36 | 0.33 |
| | Glass transition temp. (° C.) | | 124 | 124 | 123 | 124 | 123 | 123 | 125 |
| | Moisture absorption (%) | | 0.25 | 0.25 | 0.24 | 0.25 | 0.22 | 0.24 | 0.25 |
| | Adhesive strength (kgf) | | 75 | 76 | 74 | 77 | 75 | 74 | 75 |
| | Room temperature storage stability (%) | | 94 | 92 | 90 | 91 | 89 | 88 | 92 |
| Evaluation of packages | Degree of cure (Shore-D) according to curing time | 50 sec | 71 | 68 | 70 | 70 | 70 | 71 | 68 |
| | | 60 sec | 74 | 70 | 74 | 73 | 73 | 74 | 71 |
| | | 70 sec | 75 | 74 | 76 | 73 | 73 | 75 | 72 |
| | | 80 sec | 76 | 74 | 76 | 74 | 74 | 75 | 73 |
| | | 90 sec | 77 | 74 | 76 | 75 | 74 | 75 | 74 |
| | Reliability | Number of external cracks | 0 | 0 | 0 | 0 | 0 | 0 | 0 |
| | | Number of peelings | 0 | 0 | 0 | 0 | 0 | 0 | 0 |
| | | Number of semiconductors tested | 88 | 88 | 88 | 88 | 88 | 88 | 88 |

TABLE 2-continued

|  |  |  | Example | | | | Comparative Example | |
|---|---|---|---|---|---|---|---|---|
|  |  |  | 8 | 9 | 10 | 11 | 1 | 2 |
| Basic physical properties | Flowability (inch) | | 70 | 70 | 71 | 74 | 52 | 58 |
|  | Curing shrinkage (%) | | 0.35 | 0.34 | 0.35 | 0.35 | 0.42 | 0.40 |
|  | Glass transition temp. (° C.) | | 125 | 121 | 126 | 123 | 121 | 122 |
|  | Moisture absorption (%) | | 0.28 | 0.26 | 0.27 | 0.24 | 0.25 | 0.26 |
|  | Adhesive strength (kgf) | | 74 | 76 | 77 | 79 | 72 | 74 |
|  | Room temperature storage stability (%) | | 91 | 91 | 90 | 91 | 48 | 53 |
| Evaluation of packages | Degree of cure (Shore-D) according to curing time | 50 sec | 69 | 70 | 71 | 70 | 52 | 60 |
|  |  | 60 sec | 71 | 72 | 73 | 72 | 60 | 67 |
|  |  | 70 sec | 73 | 75 | 73 | 75 | 64 | 69 |
|  |  | 80 sec | 74 | 75 | 74 | 75 | 65 | 70 |
|  |  | 90 sec | 76 | 75 | 75 | 76 | 65 | 71 |
|  | Reliability | Number of external cracks | 0 | 0 | 0 | 0 | 0 | 0 |
|  |  | Number of peelings | 0 | 0 | 0 | 0 | 48 | 22 |
|  |  | Number of semiconductors tested | 88 | 88 | 88 | 88 | 88 | 88 |

As may be seen from the results in Table 2, the epoxy resin compositions of Examples 1-11 had higher flowabilities, lower curing shrinkages, and better room temperature storage stabilities than the epoxy resin compositions of Comparative Examples 1-2. Further, the epoxy resin compositions of Examples 1-11 exhibited higher degrees of cure, even in shorter curing periods of time. Further, no external cracks were observed in the packages using the epoxy resin compositions of Examples 1-11, indicating that the epoxy resin compositions had good crack resistance. Peeling was not observed between the epoxy resin compositions of Examples 1-11 and the lead frames, indicating that the epoxy resin compositions had very good moisture resistance reliability.

By way of summation and review, epoxy resin compositions for packaging electrical and electronic materials may use amine compounds such as tertiary amines, imidazoles, or the like, phosphines, phosphonium salts, etc. for the purpose of promoting curing of the resins.

With the trend toward small, lightweight, and high-performance electronic devices, high integration of semiconductor devices has been accelerated year by year. Packaging materials for semiconductor devices should exhibit fast curability (for achieving improved productivity) and good storage stability (for achieving improved handling performance during distribution and storage).

For example, an addition product of triphenylphosphine and 1,4-benzoquinone may be used as a curing accelerator. Such a curing accelerator may exhibit a curing accelerating effect in a relatively low temperature region. For example, when an epoxy resin composition is mixed with other components before curing, the epoxy resin composition may be partially cured by heat generated from the mixture system or externally applied heat. In addition, after completion of mixing, the epoxy resin composition may undergo curing even during storage at room temperature.

In the case where the epoxy resin composition takes the form of a liquid, the partial curing may bring about an increase in viscosity or deterioration of flowability. The epoxy resin composition in the form of a solid may become viscous by the partial curing. Furthermore, such a state change may not be uniform within the epoxy resin composition. As a result, curing of the epoxy resin composition at high temperature may lead to insufficient flowability of the epoxy resin composition, which may be accompanied by a deterioration in moldability of the epoxy resin composition and poor mechanical, electrical, and chemical properties of the molded product.

The use of a curing accelerator may deteriorate the storage stability of the epoxy resin composition. Thus, strict quality management should be followed when mixing various components and the epoxy resin composition should be monitored and/or strictly managed under low-temperature storage, low-temperature transport, and molding conditions. Further, the epoxy resin composition may become difficult to handle.

High-density packaging may be required in recent packaging techniques for electronic components and devices. Surface mounting type packages may tend to exhibit inferior resistance to package cracks during soldering, in comparison with pin insertion type packages. For example, in surface-mounted ICs and LSIs, an occupied volume of the devices in the package may be gradually increased, and a thickness of the package may be significantly reduced, in order to achieve high packaging density. Surface mounting type packages may be exposed to high temperature of, e.g., 200° C. or more, during soldering reflow. Thus, the presence of moisture or a volatile component in a surface mounting type package may lead to rapid expansion of the package during soldering. Such expansion may tend to cause cracks in a semiconductor module. Further, adhesion at the interface between a cured product of an epoxy resin composition and a semiconductor device or a lead frame present in a semiconductor module may be insufficient in a high-temperature reflow process, and peeling at the interface and/or deterioration of moisture resistance reliability may occur.

Sufficient moisture resistance reliability or crack resistance may not be attained in a semiconductor module including a semiconductor device packaged with a cured product of an epoxy resin composition using a curing accelerator such as an addition product of triphenylphosphonium and 1,4-benzoquinone.

The embodiments provide a latent curing accelerator that may exhibit good storage stability and sufficient flowability of an epoxy resin composition while achieving good crack resistance and high moisture resistance reliability.

The embodiments provide a quaternary phosphonium salt that helps ensure good room temperature storage stability, sufficient flowability upon curing, and high curability of an epoxy resin composition.

The embodiments provide an epoxy resin composition for encapsulating a semiconductor device that includes the quaternary phosphonium salt to help achieve good crack resistance and high moisture resistance reliability.

The embodiments provide an epoxy resin composition for encapsulating a semiconductor device and that includes a quaternary phosphonium salt as a curing accelerator.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A salt that is a solid and consisting of a quaternary phosphonium salt represented by Formula 1:

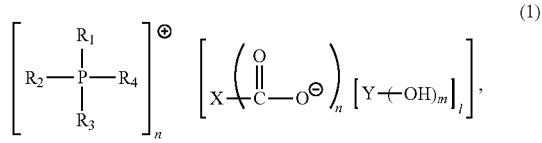

wherein:

$R_1$, $R_2$, $R_3$, and $R_4$ are each independently a substituted or unsubstituted $C_1$-$C_{30}$ hydrocarbon group or a substituted or unsubstituted $C_1$-$C_{30}$ hydrocarbon group including at least one heteroatom;

X is a substituted or unsubstituted $C_1$-$C_{30}$ hydrocarbon group or a substituted or unsubstituted $C_1$-$C_{30}$ hydrocarbon group including at least one heteroatom;

Y is a substituted or unsubstituted $C_1$-$C_{30}$ hydrocarbon group or Si substituted with one to three substituted or unsubstituted $C_1$-$C_{30}$ hydrocarbon groups, the substituted $C_1$ to $C_{30}$ hydrocarbon groups being each independently substituted with a halogen atom, a hydroxyl group, a $C_1$-$C_{10}$ alkyl group, a $C_1$-$C_{10}$ haloalkyl group, a $C_6$-$C_{10}$ aryl group, a $C_1$-$C_{10}$ alkoxy group, or a combination thereof;

n and m are each independently an integer of 1 to 6, provided that when Y is Si, a sum of m and a number of substituents on the Si is a maximum of 4; and l is a number greater than 0 and up to 6.

2. The salt as claimed in claim 1, wherein $R_1$, $R_2$, $R_3$, and $R_4$ are each independently a substituted or unsubstituted benzene group.

3. The salt as claimed in claim 1, wherein X is a substituted or unsubstituted benzene group.

4. The salt as claimed in claim 1, wherein Y is a substituted or unsubstituted benzene group, a substituted or unsubstituted naphthalene group, or Si substituted with one to three substituted or unsubstituted benzene groups.

5. The salt as claimed in claim 1, wherein n is 2.

6. The salt as claimed in 1, wherein m is 2 or 3.

7. The salt as claimed in claim 1, wherein l is 2, 3, or 4.

8. A quaternary phosphonium salt represented by one of Formulae 1a to 1k:

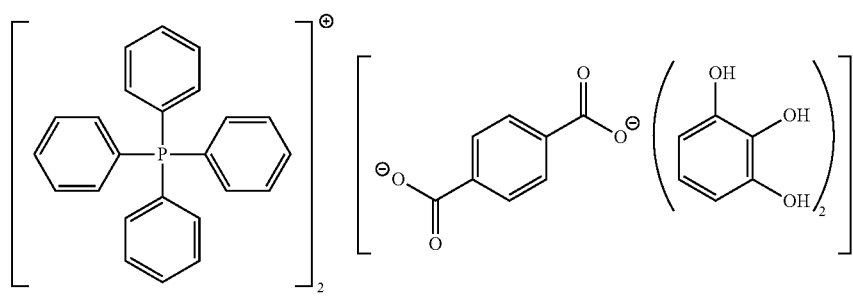

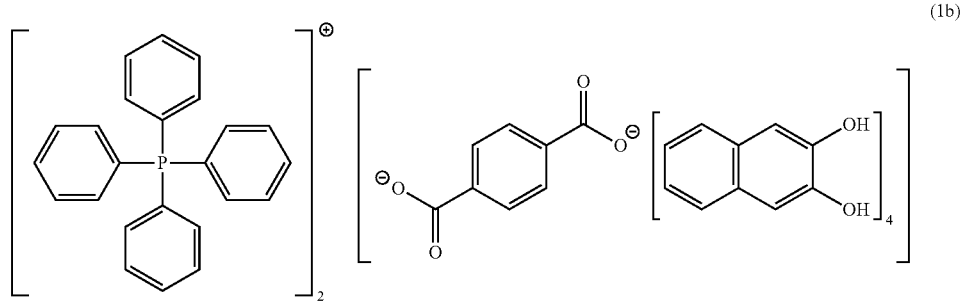

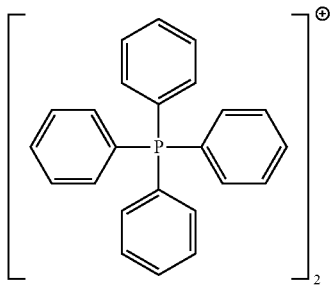 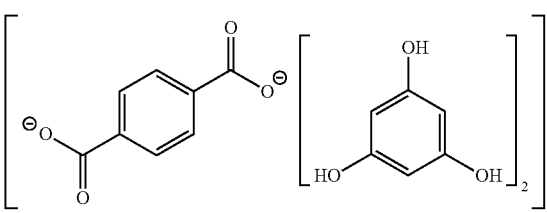
(1c)
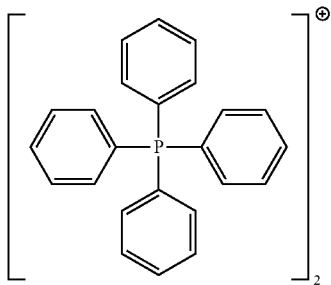 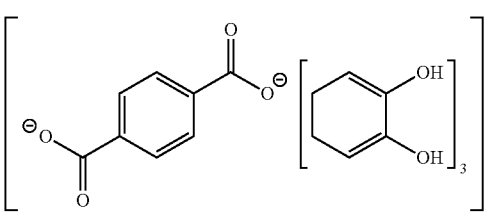
(1d)
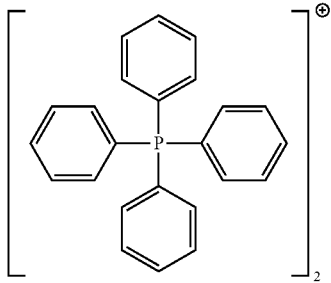 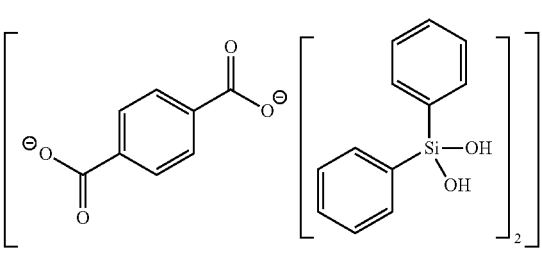
(1e)
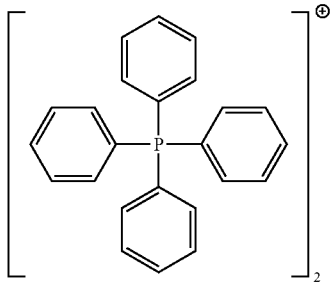 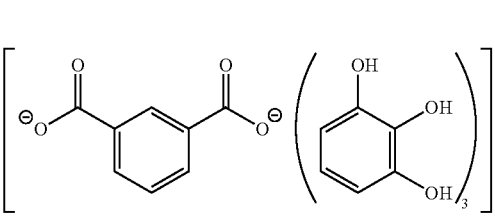
(1f)
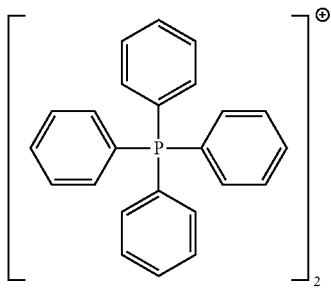 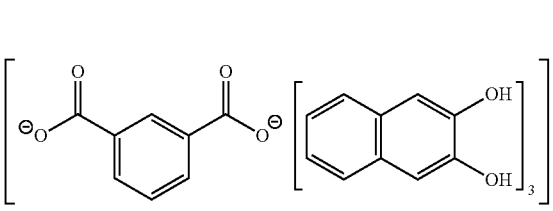
(1g)

-continued
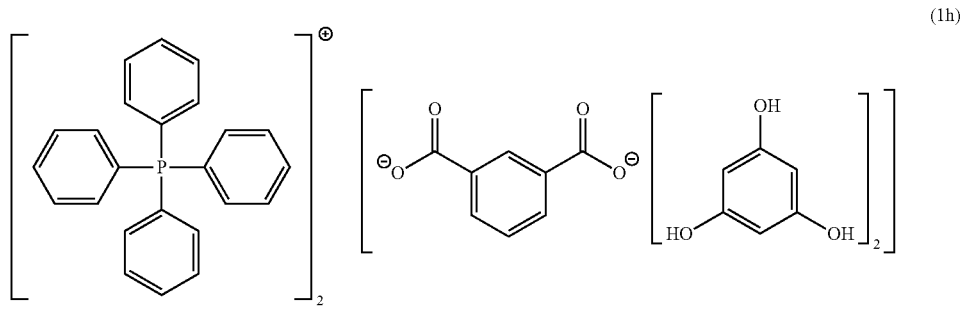
(1h)
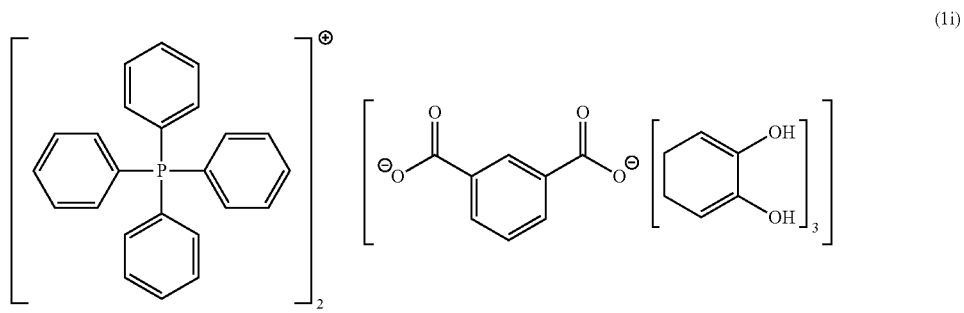
(1i)
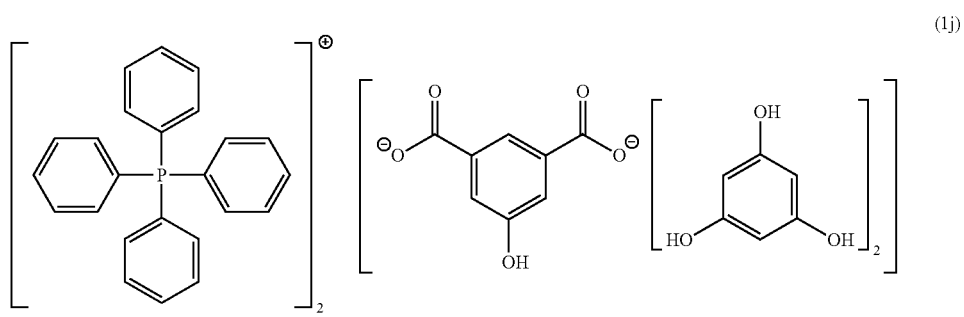
(1j)
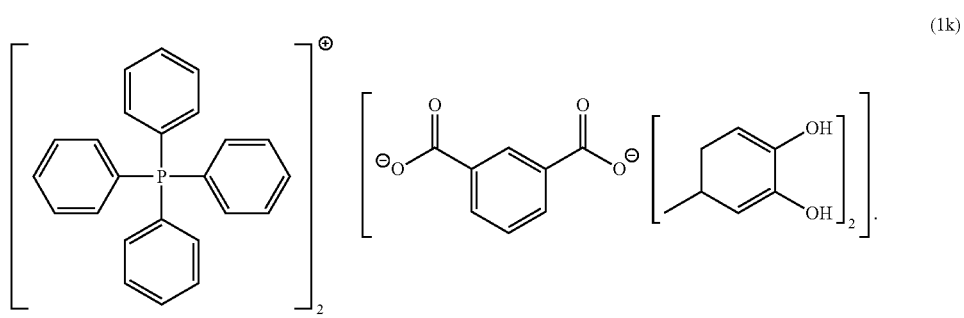
(1k)

9. An epoxy resin composition, comprising:
an epoxy resin,
a curing agent,
a curing accelerator, and
an inorganic filler,
wherein the curing accelerator includes a quaternary phosphonium salt represented by one of Formulae 1a to 1k:
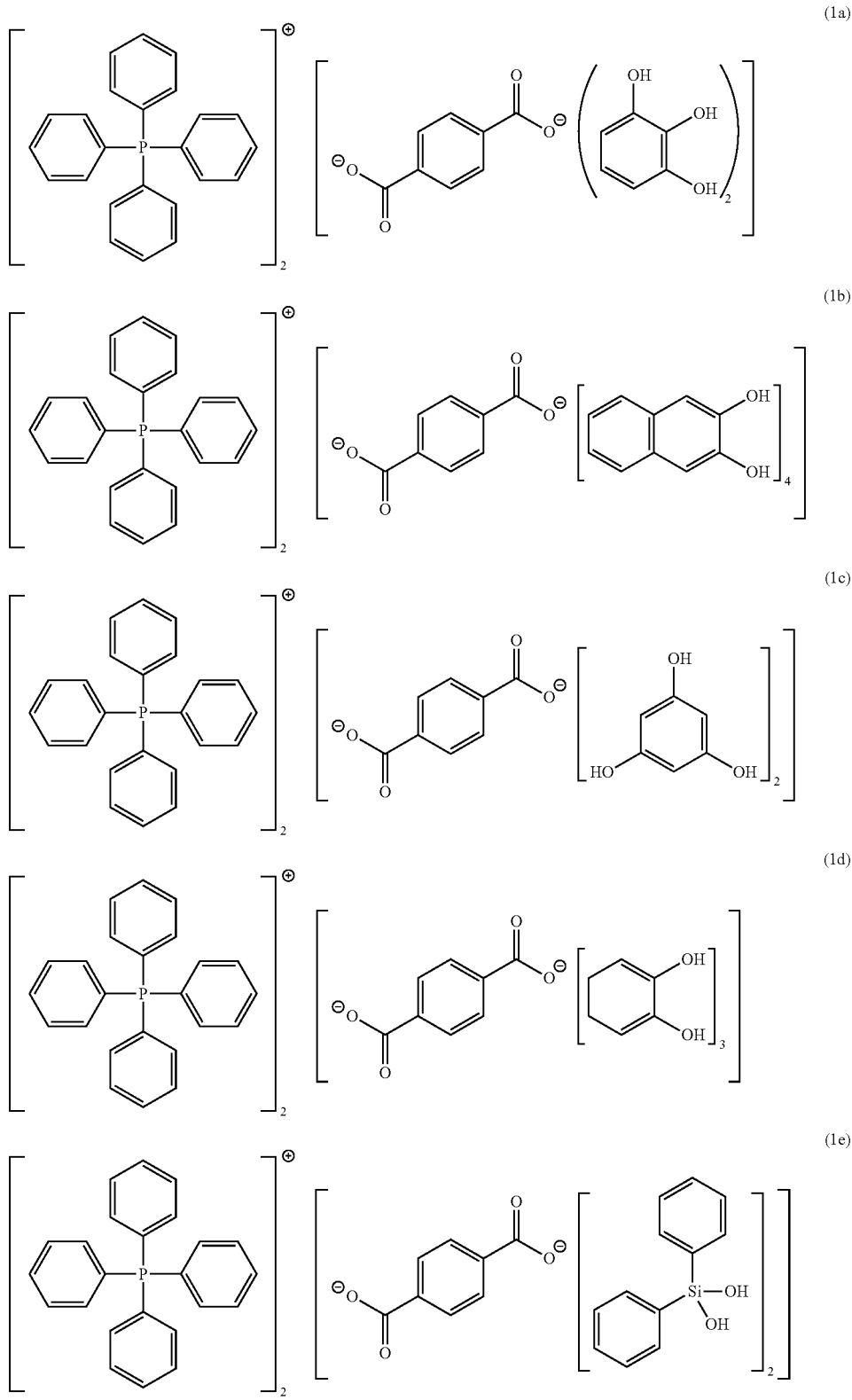

-continued
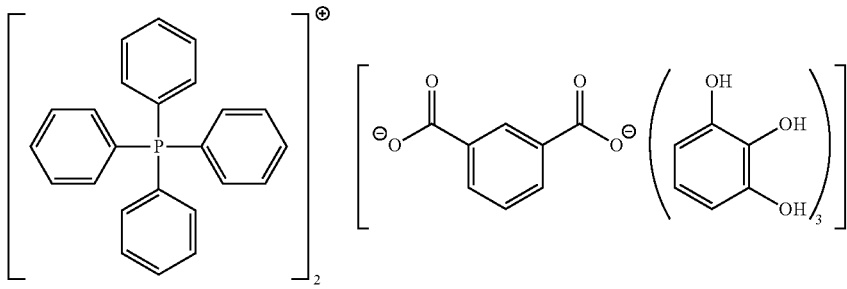
(1f)
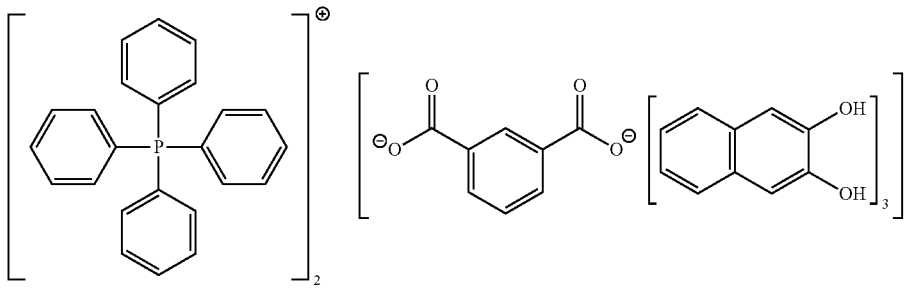
(1g)
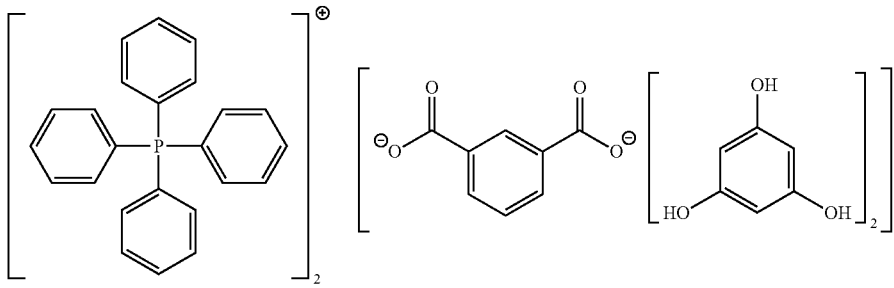
(1h)
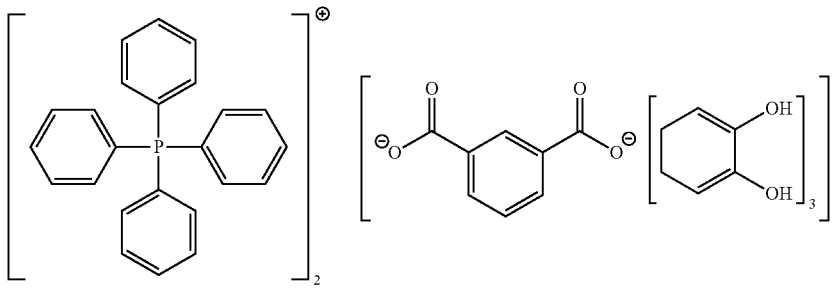
(1i)
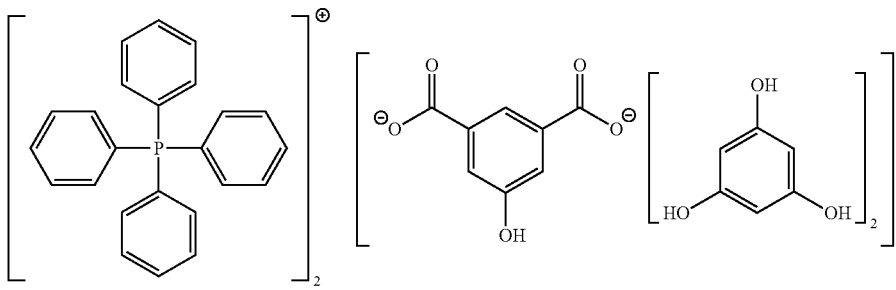
(1j)

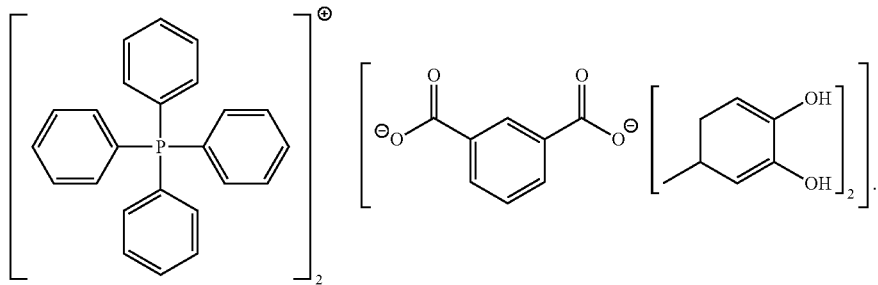

(1k)

10. The epoxy resin composition as claimed in claim 9, wherein the epoxy resin composition includes:
about 1% to about 20% by weight of the epoxy resin,
about 1% to about 20% by weight of the curing agent,
about 0.001% to about 2% by weight of the curing accelerator, and
about 70% to about 95% by weight of the inorganic filler.

11. The epoxy resin composition as claimed in claim 9, wherein the epoxy resin includes at least one of an epoxy resin obtained by epoxidation of condensation products of phenol or alkyl phenols and hydroxybenzaldehyde, a phenol novolac type epoxy resin, a cresol novolac type epoxy resin, a polyfunctional epoxy resin, a naphthol novolac type epoxy resin, a novolac type epoxy resin of bisphenol A/bisphenol F/bisphenol AD, a glycidyl ether of bisphenol A/bisphenol F/bisphenol AD, a bishydroxybiphenyl-based epoxy resin, a dicyclopentadiene-based epoxy resin, a biphenyl type epoxy resin, a polycyclic aromatic-modified epoxy resin, a bisphenol A type epoxy resin, an ortho-cresol novolac type epoxy resin, a phenol aralkyl type epoxy resin, or a naphthalene-based epoxy resin.

12. The epoxy resin composition as claimed in claim 9, wherein the curing agent includes at least one of a phenol aralkyl type phenolic resin, a xyloc type phenolic resin, a phenol novolac type phenolic resin, a cresol novolac type phenolic resin, a naphthol type phenolic resin, a terpene type phenolic resin, a polyfunctional phenolic resin, a polycyclic aromatic phenolic resin, a dicyclopentadiene-based phenolic resin, a terpene-modified phenolic resin, a dicyclopentadiene-modified phenolic resin, a novolac type phenolic resin synthesized from bisphenol A and resorcinol, a polyhydric phenolic compound, an acid anhydride, a metaphenylenediamine, a diaminodiphenylmethane, or a diaminodiphenylsulfone.

13. The epoxy resin composition as claimed in claim 9, wherein the epoxy resin and the curing agent are present in amounts such that a ratio of an epoxy equivalent weight of the epoxy resin to a phenolic hydroxyl equivalent weight or an amine equivalent weight of the curing agent is about 0.5:1 to about 2:1.

* * * * *